(12) United States Patent
Viola et al.

(10) Patent No.: US 9,113,875 B2
(45) Date of Patent: *Aug. 25, 2015

(54) FLEXIBLE SURGICAL STAPLER WITH MOTOR IN THE HEAD

(71) Applicant: Covidien LP, Mansfield, MA (US)

(72) Inventors: Frank Viola, Sandy Hook, CT (US); John W. Beardsley, Wallingford, CT (US); Teddy R. Bryant, San Francisco, CA (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/479,422

(22) Filed: Sep. 8, 2014

(65) Prior Publication Data

US 2014/0374464 A1 Dec. 25, 2014

Related U.S. Application Data

(63) Continuation of application No. 12/814,833, filed on Jun. 14, 2010, now Pat. No. 8,827,134.

(60) Provisional application No. 61/218,489, filed on Jun. 19, 2009.

(51) Int. Cl.
*A61B 17/04* (2006.01)
*A61B 17/10* (2006.01)
*A61B 17/068* (2006.01)
*A61B 17/072* (2006.01)
*A61B 17/00* (2006.01)
*A61B 17/29* (2006.01)

(52) U.S. Cl.
CPC ......... *A61B 17/068* (2013.01); *A61B 17/07207* (2013.01); *A61B 2017/003* (2013.01); *A61B 2017/00017* (2013.01); *A61B 2017/00022* (2013.01); *A61B 2017/00309* (2013.01); *A61B 2017/00327* (2013.01); *A61B 2017/00398* (2013.01); *A61B 2017/00433* (2013.01); *A61B 2017/07271* (2013.01); *A61B 2017/07278* (2013.01); *A61B 2017/2905* (2013.01); *A61B 2017/2927* (2013.01); *A61B 2017/2932* (2013.01)

(58) Field of Classification Search
CPC ...................... A61B 2017/2927; A61B 17/068
USPC ............................................. 227/175.1–182.1
See application file for complete search history.

(56) References Cited

U.S. PATENT DOCUMENTS

| | | |
|---|---|---|
| 5,156,609 A | 10/1992 | Nakao et al. |
| 5,389,102 A | 2/1995 | Green et al. |
| 5,431,323 A | 7/1995 | Smith et al. |
| 5,433,721 A | 7/1995 | Hooven et al. |

(Continued)

FOREIGN PATENT DOCUMENTS

| | | |
|---|---|---|
| EP | 1785097 | 5/2007 |
| EP | 1884201 A1 | 2/2008 |

(Continued)

*Primary Examiner* — Robert Long

(57) ABSTRACT

A surgical stapler having a remote motorized staple head is provided and generally includes a handle having a control button and a highly flexible cable extending distally from the handle. A housing incorporating a staple assembly is affixed to a distal end of the flexible cable. The housing may incorporate articulating structure to position the staple assembly relative to the remainder of the housing.

17 Claims, 35 Drawing Sheets

(56) References Cited

U.S. PATENT DOCUMENTS

| | | |
|---|---|---|
| 5,779,130 A | 7/1998 | Alesi et al. |
| 5,871,135 A | 2/1999 | Williamson, IV et al. |
| 5,954,259 A | 9/1999 | Viola et al. |
| 6,343,731 B1 | 2/2002 | Adams et al. |
| 6,644,532 B2 | 11/2003 | Green et al. |
| 6,685,079 B2 | 2/2004 | Sharma et al. |
| 7,077,856 B2 | 7/2006 | Whitman |
| 7,159,750 B2 | 1/2007 | Racenet et al. |
| 7,380,695 B2 | 6/2008 | Doll et al. |
| 7,404,508 B2 | 7/2008 | Smith et al. |
| 7,410,086 B2 | 8/2008 | Ortiz et al. |
| 7,431,188 B1 | 10/2008 | Marczyk |
| 7,431,189 B2 * | 10/2008 | Shelton et al. ............. 227/176.1 |
| 7,434,716 B2 | 10/2008 | Viola |
| 7,434,717 B2 | 10/2008 | Shelton, IV et al. |
| 7,543,730 B1 | 6/2009 | Marczyk |
| 7,568,603 B2 | 8/2009 | Shelton, IV et al. |
| 7,617,961 B2 | 11/2009 | Viola |
| 7,637,905 B2 | 12/2009 | Saadat et al. |
| 7,641,095 B2 | 1/2010 | Viola |
| 7,708,182 B2 | 5/2010 | Viola |
| 7,736,374 B2 | 6/2010 | Vaughan et al. |
| 7,740,159 B2 | 6/2010 | Shelton, IV et al. |
| 7,744,613 B2 | 6/2010 | Ewers et al. |
| 7,766,207 B2 | 8/2010 | Mather et al. |
| 7,810,693 B2 | 10/2010 | Broehl et al. |
| 7,819,884 B2 | 10/2010 | Lee et al. |
| 7,854,738 B2 | 12/2010 | Lee et al. |
| 7,861,906 B2 | 1/2011 | Doll et al. |
| 7,862,502 B2 | 1/2011 | Pool et al. |
| 7,866,527 B2 | 1/2011 | Hall et al. |
| 7,879,070 B2 | 2/2011 | Ortiz et al. |
| 7,909,220 B2 | 3/2011 | Viola |
| 7,918,230 B2 | 4/2011 | Whitman et al. |
| 7,922,061 B2 | 4/2011 | Shelton, IV et al. |
| 7,922,063 B2 | 4/2011 | Zemlok et al. |
| 7,922,758 B2 | 4/2011 | Gregorich et al. |
| 7,959,642 B2 | 6/2011 | Nobis et al. |
| 7,992,758 B2 | 8/2011 | Whitman et al. |
| 8,021,373 B2 | 9/2011 | Whitman et al. |
| 8,033,442 B2 | 10/2011 | Racenet et al. |
| 8,034,077 B2 | 10/2011 | Smith et al. |
| 8,061,577 B2 | 11/2011 | Racenet et al. |
| 8,091,753 B2 | 1/2012 | Viola |
| 8,096,460 B2 | 1/2012 | Blier et al. |
| 8,113,410 B2 | 2/2012 | Hall et al. |
| 8,827,134 B2 | 9/2014 | Viola et al. |
| 2004/0050902 A1 | 3/2004 | Green et al. |
| 2006/0047308 A1 | 3/2006 | Ortiz et al. |
| 2007/0023477 A1 | 2/2007 | Whitman et al. |
| 2007/0073341 A1 | 3/2007 | Smith et al. |
| 2007/0187453 A1 | 8/2007 | Smith et al. |
| 2007/0282356 A1 | 12/2007 | Sonnenschein et al. |
| 2008/0029575 A1 | 2/2008 | Shelton et al. |
| 2008/0029576 A1 | 2/2008 | Shelton et al. |
| 2008/0169327 A1 | 7/2008 | Shelton et al. |
| 2008/0169332 A1 | 7/2008 | Shelton et al. |
| 2008/0169333 A1 | 7/2008 | Shelton et al. |
| 2008/0277447 A1 | 11/2008 | Smith et al. |
| 2009/0090764 A1 | 4/2009 | Viola |
| 2009/0289096 A1 | 11/2009 | Shelton, IV et al. |
| 2011/0118707 A1 | 5/2011 | Burbank |
| 2012/0074200 A1 | 3/2012 | Schmid et al. |
| 2012/0074201 A1 | 3/2012 | Baxter, III et al. |
| 2012/0080475 A1 | 4/2012 | Smith et al. |
| 2012/0104071 A1 | 5/2012 | Bryant |

FOREIGN PATENT DOCUMENTS

| | | |
|---|---|---|
| EP | 1980214 A2 | 10/2008 |
| EP | 2090240 A1 | 8/2009 |

\* cited by examiner

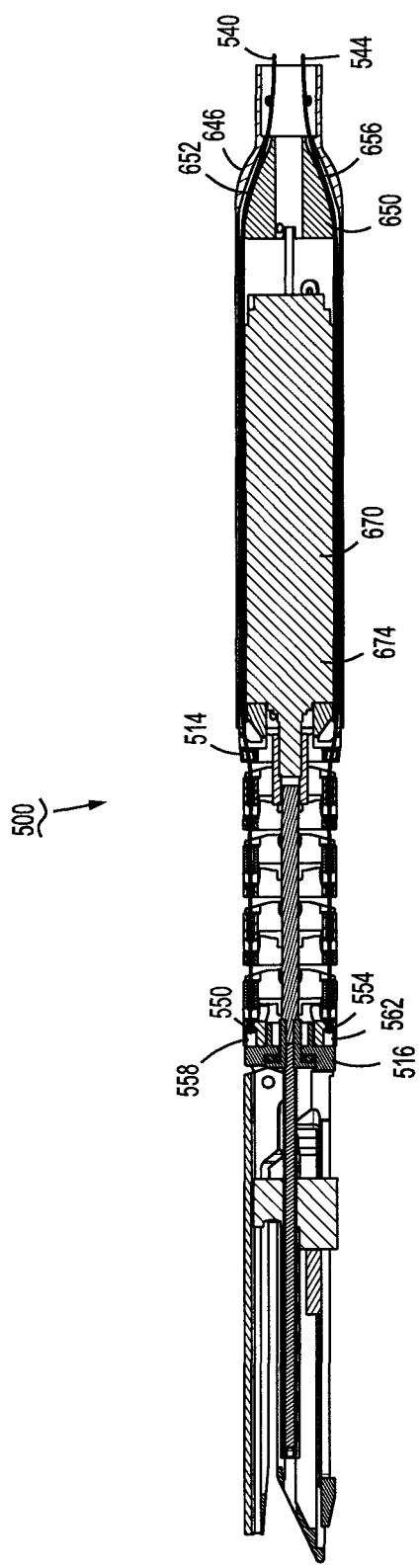
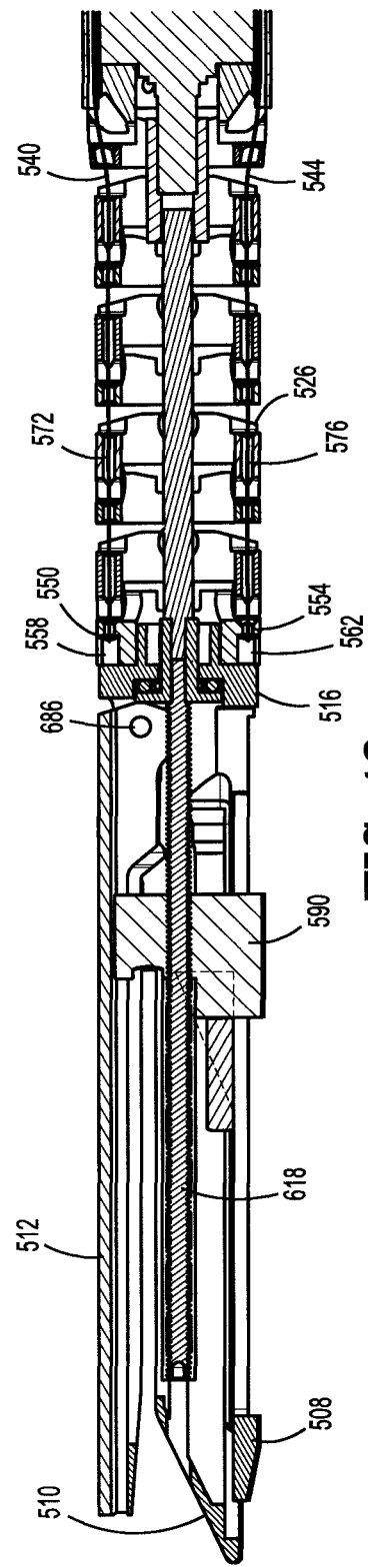

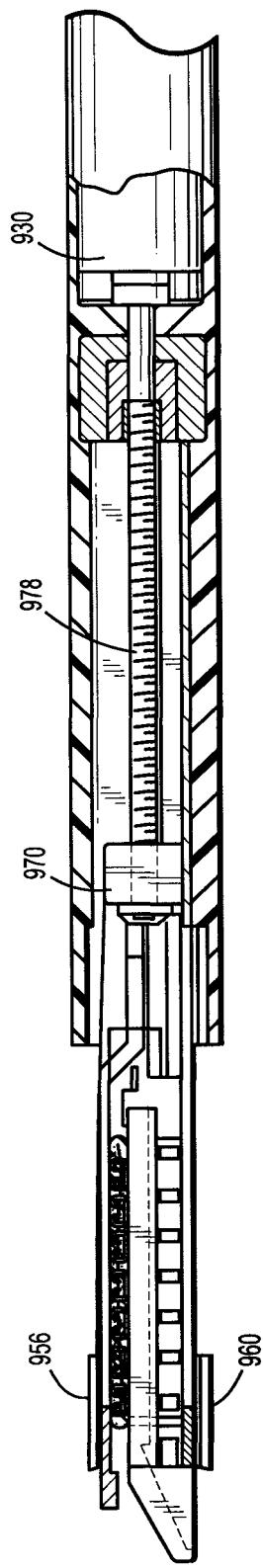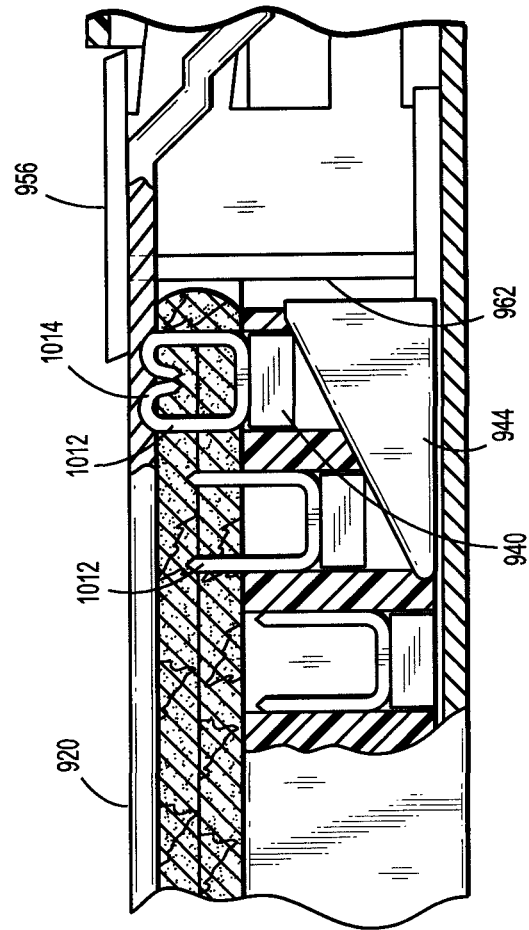

FLEXIBLE SURGICAL STAPLER WITH MOTOR IN THE HEAD

CROSS-REFERENCE TO RELATED APPLICATIONS

The present application is a continuation application of U.S. application Ser. No. 12/814,833 filed Jun. 14, 2010, now U.S. Pat. No. 8,827,134, which claims priority to, and the benefit of, U.S. Provisional Application Ser. No. 61/218,489 filed Jun. 19, 2009, the entire contents of each of which are hereby incorporated by reference.

BACKGROUND

1. Technical Field

The present disclosure relates to flexible surgical staplers having a motor in the end effector. More particularly, the present disclosure relates to flexible surgical staplers having a highly flexible cable between an actuator and stapler driving motor located in the stapler head.

2. Background of Related Art

Various surgical stapling devices are known in the art which are designed to be passed through a port and into a body cavity to perform a stapling procedure on tissue. These devices generally include a handle having a rigid elongate member extending distally therefrom. A staple assembly is provided on the distal end of the elongate member to staple tissue and sever the tissue between rows of staples.

In general, the rigid elongate member is necessary to accommodate actuation structures such as, for example, rods, coaxial shafts, etc. This may limit the ability to manipulate the staple assembly relative to the tissue desired to be operated upon. Advancements in the surgical stapling devices incorporate articulation structure interposed intermediate separate rigid elongate shafts are members to orient the staple assembly. However, these devices still limit the range of flexibility between the staple assembly and the associated handle.

Thus, it is desirable to provide a surgical stapler having a high degree of flexibility between a remote stapler assembly and an associated handle or actuator. It is further desirable to provide a surgical stapler having a further degree of flexibility within the stapler head itself.

SUMMARY

There is disclosed a surgical stapler having a remote motorized stapling head. The surgical stapler generally includes a handle having a control button and a highly flexible elongate member extending distally from the handle. A staple assembly is provided on the distal end of the flexible elongate member. A housing containing a motor is provided and is positioned between the flexible elongate member and the staple assembly. An articulating section is positioned intermediate the housing and the staple assembly.

In one embodiment, the articulating section incorporates a universal joint. A flexible cover is provided over the universal joint to protect surrounding tissue.

An auxiliary collar is provided to be positioned over the housing and may incorporate various additional functions. The auxiliary collar can provide optical, cautery or other auxiliary functions to the staple assembly.

In another embodiment, the articulating section incorporates a flexible gooseneck structure.

In still a further alternative embodiment, the articulating section incorporates a plurality of interconnecting links which are controlled by guide wires and allow the staple assembly to be moved vertically and horizontally relative to the housing.

There is also provided a handle assembly for manipulating a plurality of guide wires. The handle assembly generally includes a body portion having a pistol grip and a trigger for actuating a motor in a staple head utilized with the disclosed handle assembly. The handle assembly includes a first knob for reciprocating a first pair of guide wires and a second knob for reciprocating a second pair of guide wires. A third knob is provided for simultaneously reciprocating both first and second pairs of guide wires.

There is also disclosed a surgical stapling instrument having a handle including a control button, and elongate flexible member extending distally from the handle and a housing and staple assembly positioned at a distal end of the flexible elongate member.

In one embodiment, the surgical stapling instrument incorporates an articulating section positioned between a proximal portion of the housing containing a motor and a distal portion of the housing incorporating the staple assembly. A flexible drive shaft extends between the motor and the staple assembly.

In a further embodiment, the surgical stapling instrument incorporates an articulating section located immediately proximal to a staple cartridge and a handle of a staple assembly. A portion of the actuating components of the staple assembly are formed from flexible materials extending through the articulating section.

DESCRIPTION OF THE DRAWINGS

Various embodiments of the presently disclosed remote motorized stapler heads are disclosed herein with reference to the drawings, wherein:

FIG. 18 is a cross-sectional view of the remote motorized stapler head of FIG. 16;

FIG. 19 is an enlarged cross-sectional view of the remote motorized stapler head of FIG. 16;

FIG. 32 is a side view, partially shown in section, of the stapler head during further actuation to staple the captured tissue;

FIG. 33 is an enlarged partial side view of the stapler head during the stapling of the captured tissue;

DETAILED DESCRIPTION OF THE EMBODIMENTS

Embodiments of the presently disclosed remote motorized stapler heads and surgical staplers will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Figure 1:
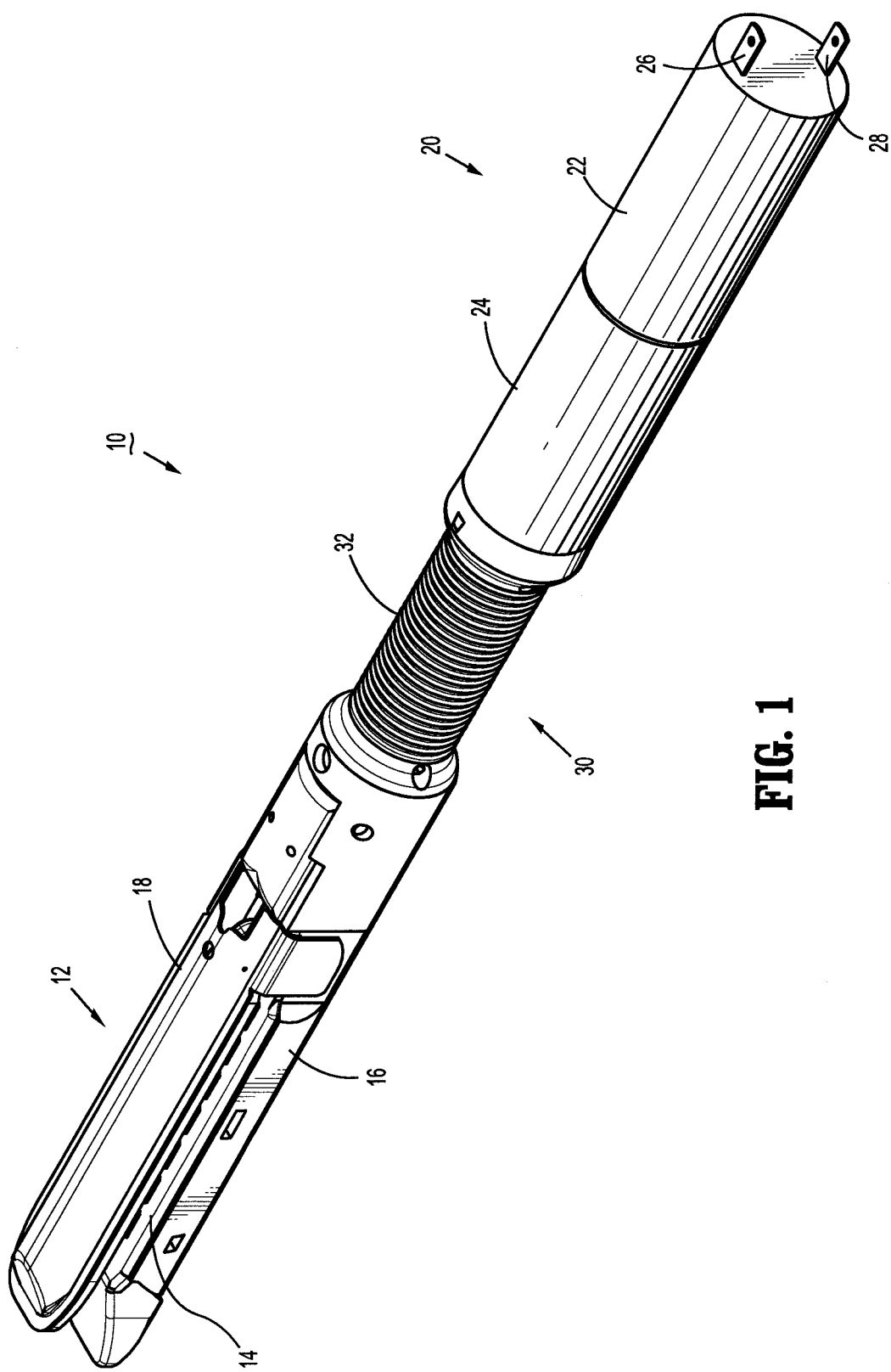
FIG. 1 is a perspective view of one embodiment of a remote motorized stapler head.

Referring to FIGS. 1-6, and initially to FIG. 1, there is disclosed a remote, motorized stapler head 10 for use in a surgical instrument. Stapler head 10 is provided to enhance the flexibility of a surgical stapler when used in various areas of the body and is designed to be inserted through a cannula. Stapler head 10 can then be manipulated within the body while the actuating mechanism (not shown) remains outside the body. Stapler head 10 is connected to the actuating mechanism by a pair of highly flexible cables or wires.

Stapler head 10 generally includes a staple assembly 12 including a staple cartridge 14 positioned in a channel member 16. An anvil assembly 18 is pivotally mounted to channel member 16 and is movable between an open position spaced apart from staple cartridge 14 to a closed position substantially adjacent staple cartridge 14.

A motor assembly 20 is provided to move anvil assembly 18 between the open and closed positions and to fire staples 62, 64 (FIG. 4) from staple cartridge 14, through tissue and into anvil assembly 18 in a manner described in more detail herein below. Motor assembly 20 includes a motor 22 connected to a gearbox 24. Electrical contacts 26 and 28 are on motor 22 and are provided to engage wires of a remote actuator/power source (not shown). An articulation section 30 is provided intermediate staple assembly 12 and motor assembly 20 to provide a greater degree of flexibility to stapler head 10. By allowing for articulation between motor assembly 20 and staple assembly 12, a surgeon can better manipulate staple head 10 around body organs to properly position staple assembly 12 relative to the tissue to be stapled. This is particularly desirable where, as here, the associated surgical stapler includes a remote actuator and a highly flexible and thin connector cable connecting the actuator to stapler head 10. An articulation cover 32 is included in articulation section 30 to prevent snagging of tissue as staple assembly 12 is manipulated relative to motor assembly 20.

Figure 42:
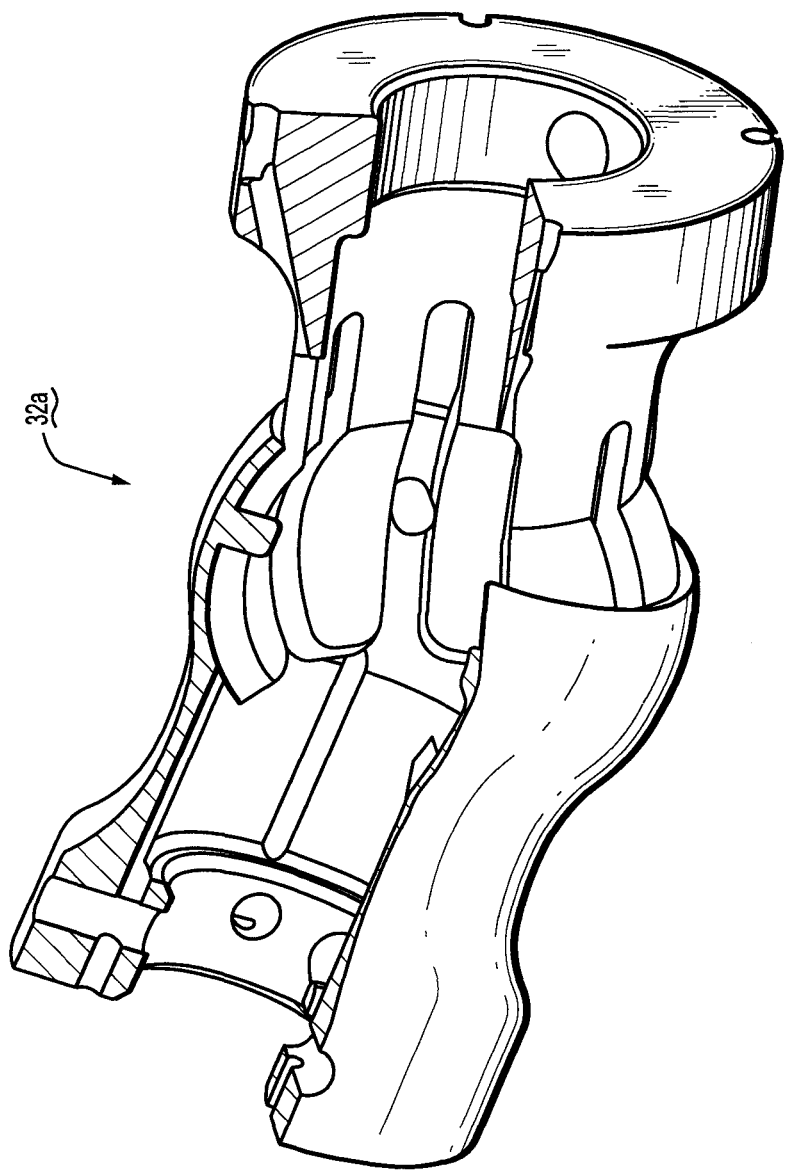
FIG. 42 is a perspective view, partially shown in section, of an articulated knuckle.

In an alternate embodiment, as shown in FIG. 42, the articulation section may include an articulating knuckle joint 32A, i.e., a ball and socket joint. Articulating knuckle joint 32A may be used in place of articulation cover 32 to prevent snagging of tissue. Further, articulating knuckle joint 32A may be configured to permit 360 degree articulation of staple assembly 12 with respect to motor assembly 20.

Figure 2:
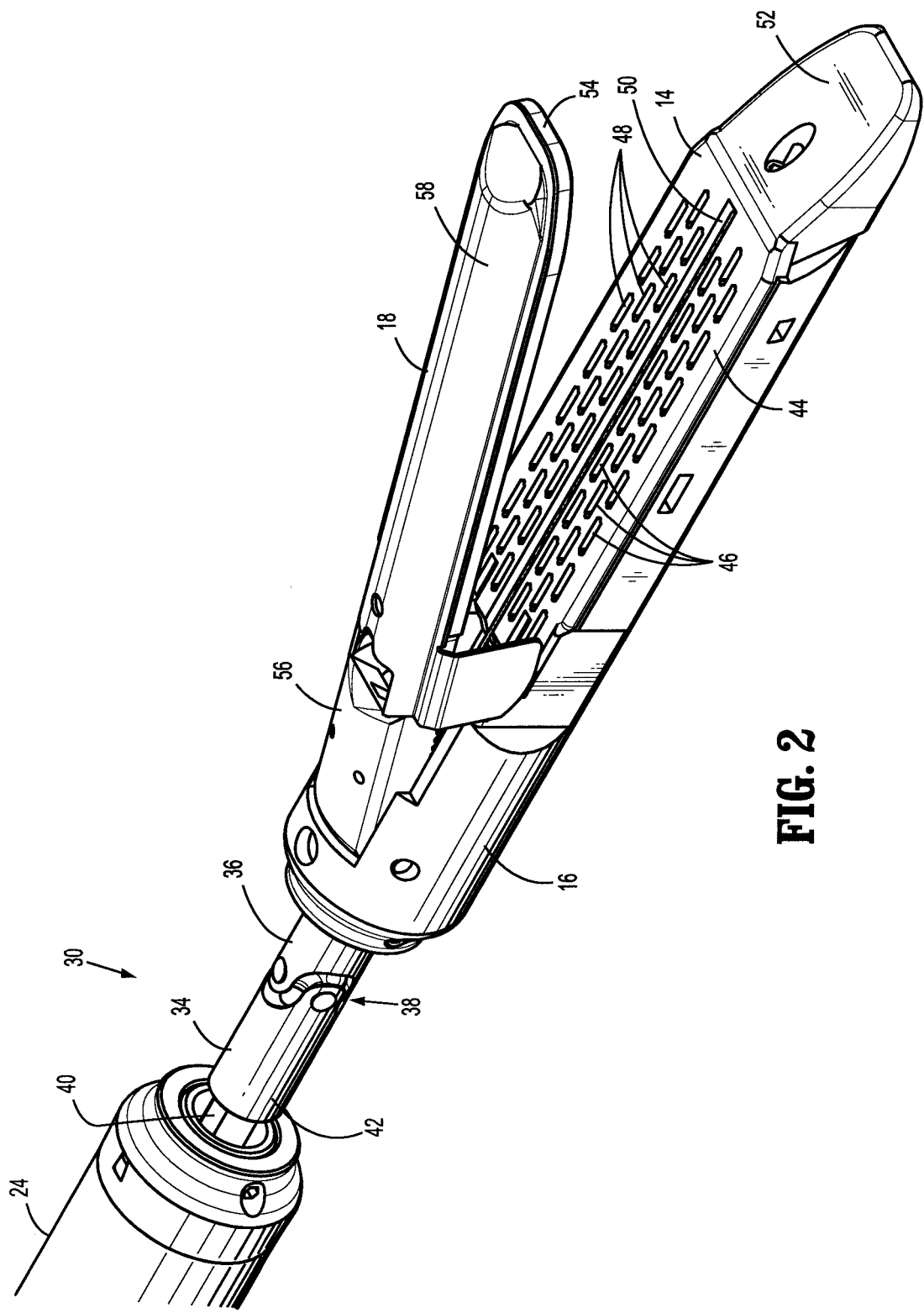
FIG. 2 is a perspective view of the remote motorized stapler head with an articulation cover removed.
Figure 3:
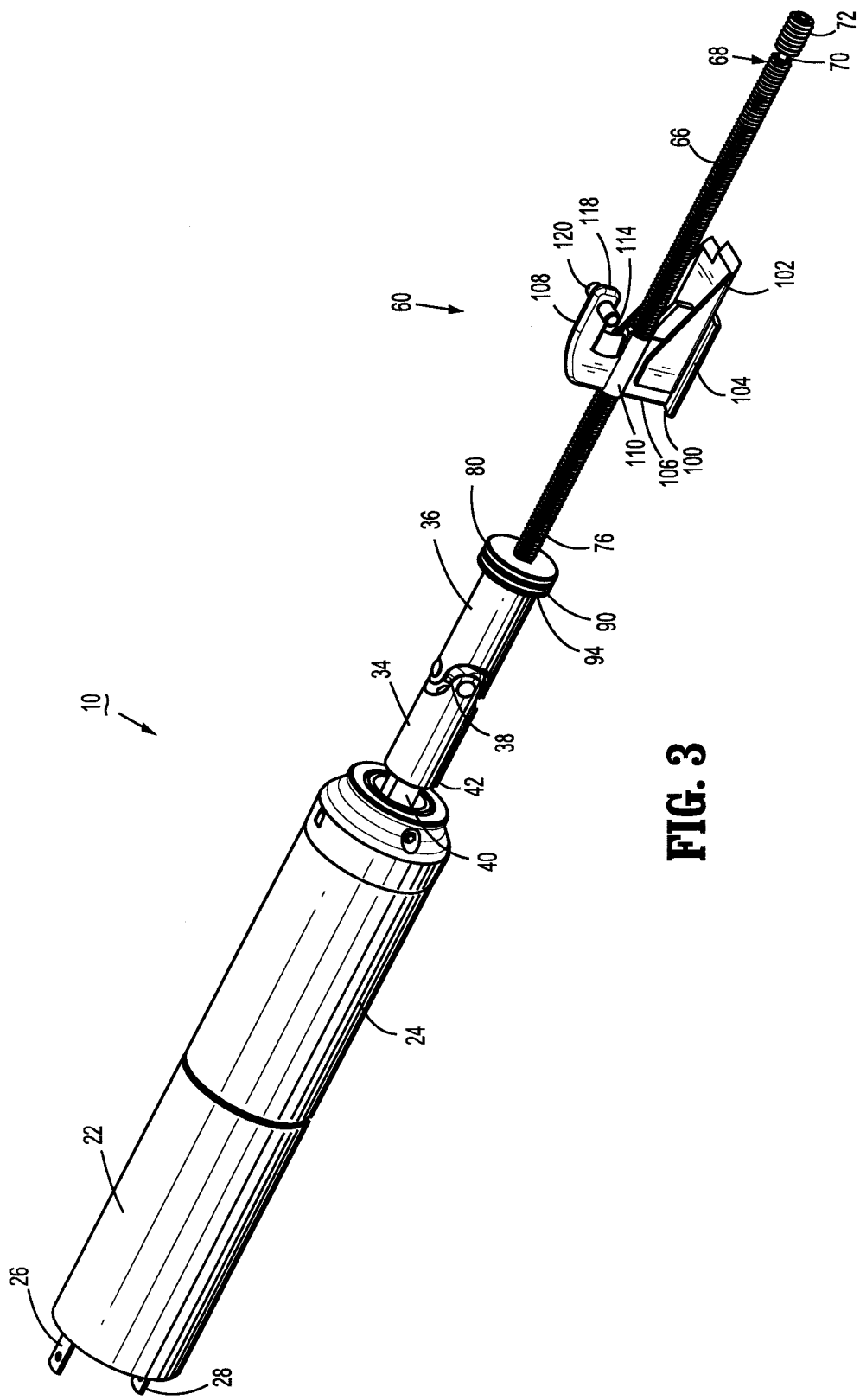
FIG. 3 is a perspective view of the remote motorized stapler head with a staple cartridge and an anvil removed.

Referring now to FIGS. 2 and 3, in order to bend or move staple assembly 12 relative to motor assembly 20, articulation section 30 includes a proximal articulation shaft 34 and a distal articulation shaft 36. Proximal articulation shaft 34 is connected to distal articulation shaft 36 by a universal joint 38, which permits 360 degree articulation of distal articulation shaft 36 with respect to proximal articulation shaft 34. Proximal and distal articulation shafts 34 and 36 also transfer power from gear box 24 through articulation section 30 and to staple assembly 12. Specifically, a drive shaft 40 of gear box 24 is keyed into a proximal end 42 of proximal articulation shaft 34.

Figure 43:
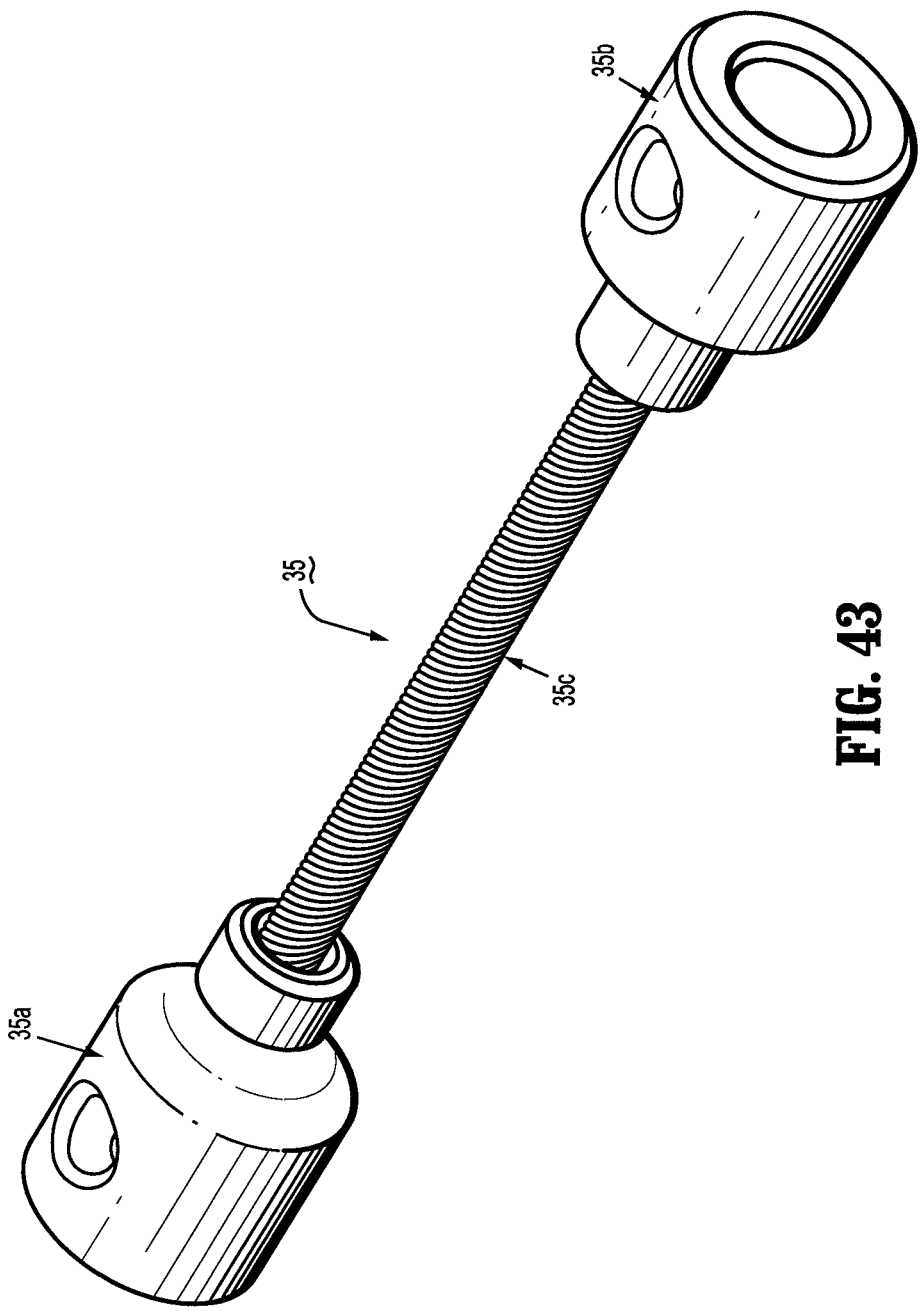
FIG. 43 is a perspective view of a flexible shaft assembly.
Figure 44:
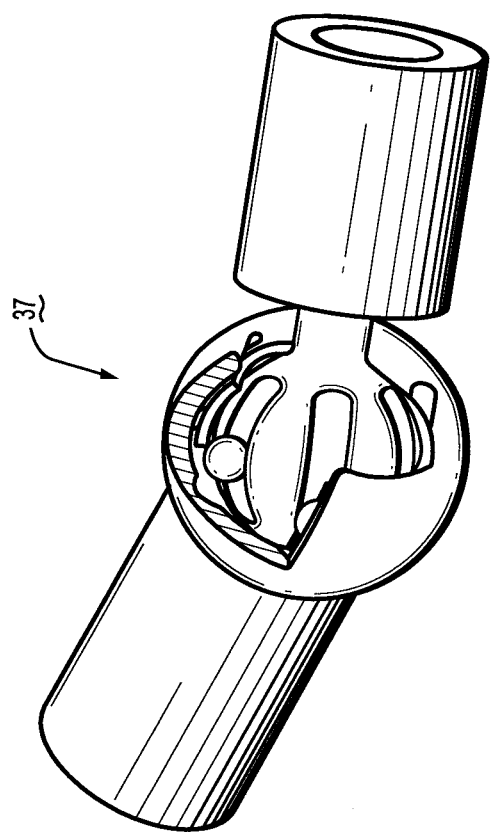
FIG. 44 is a perspective view, partially shown in section, of the articulated knuckle.

In an alternative embodiment, as shown in FIG. 43, a flexible shaft assembly 35 having a proximal portion 35a, a distal portion 35b, and a central portion 35c may be used in place of proximal articulation shaft 34, distal articulation shaft 36, and universal joint 38. Central portion 35c of flexible shaft assembly 35 may be a flexible multistrand wound cable configured to permit flexion, or articulation of distal portion 35b with respect to proximal portion 35a. In another embodiment, as shown in FIG. 44, in order to bend or move staple assembly 12 relative to motor assembly 20, articulation section 30 may include a constant-velocity (CV) joint assembly 37 (FIG. 44), e.g., a constant-velocity knuckle joint, to allow transmission of rotation through articulation section 30 at variable angles, e.g., through 360 degrees, instead of proximal articulation shaft 34, distal articulation shaft 36, and universal joint 38.

Referring for the moment to FIG. 2, and as noted above, staple assembly 12 generally includes staple cartridge 14 mounted in channel 16 and anvil assembly 18 pivotally mounted to channel 16. Staple cartridge 14 is formed of a plastic material, body portion 44 having longitudinally extending rows of staple containing pockets 46 and 48. A longitudinally extending knife channel 50 is formed in body portion 44 between rows of staple containing pockets 46 and 48 for passage of a knife blade as described below. A tapered distal tip 52 extends from body portion 44 to facilitate manipulation of staple assembly 12 about tissue.

Anvil assembly 18 includes an anvil plate 54 mounted to an anvil base 56. An anvil cover 48 is also mounted to anvil base 56 and overlies anvil plate 54. Anvil plate 54 includes rows of anvil clinching pockets (not shown) which correspond to rows of staple containing pockets 46 and 48.

Figure 4:
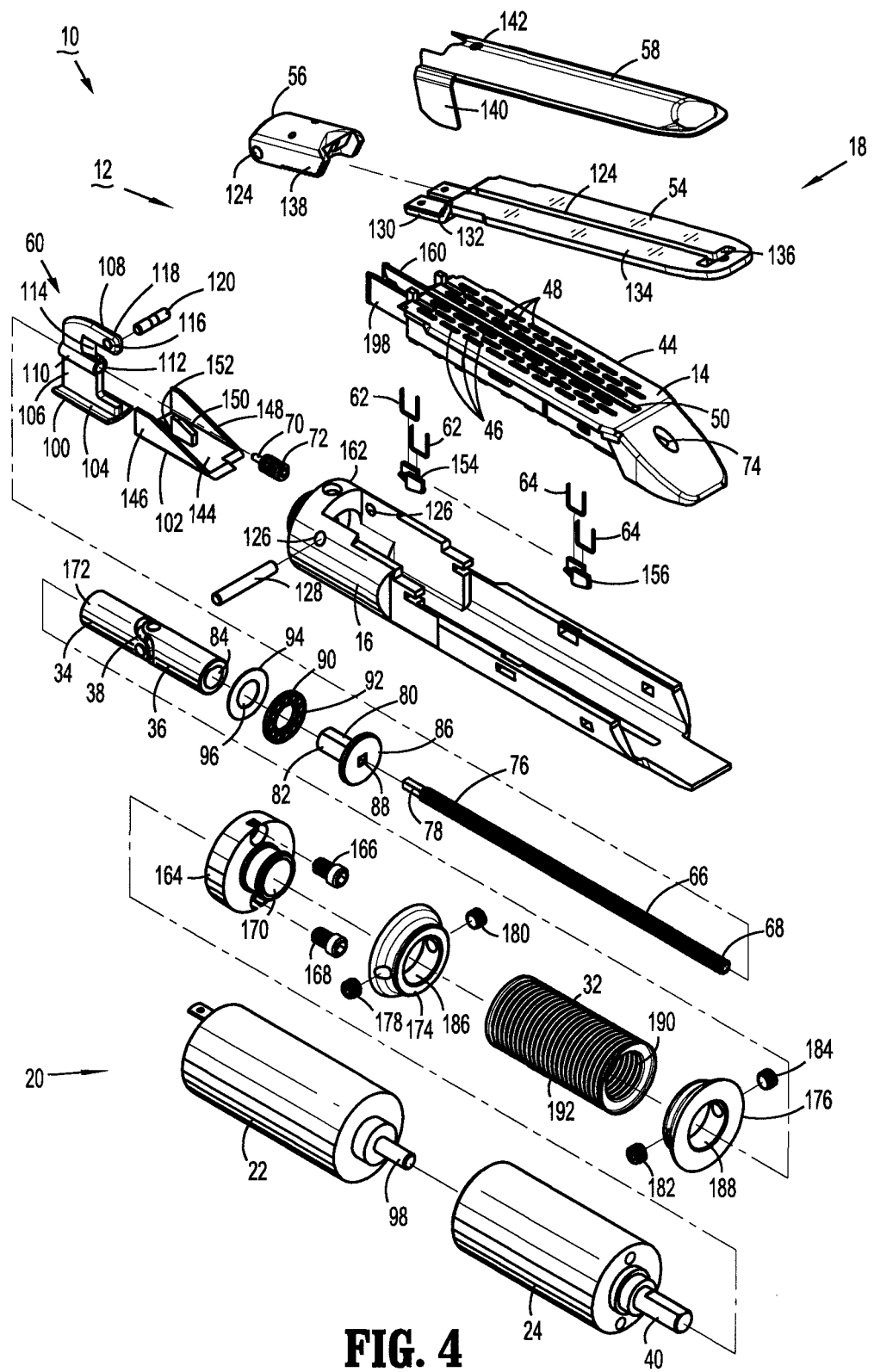
FIG. 4 is a perspective view, with parts separated, of the remote motorized stapler head.
Figure 5:
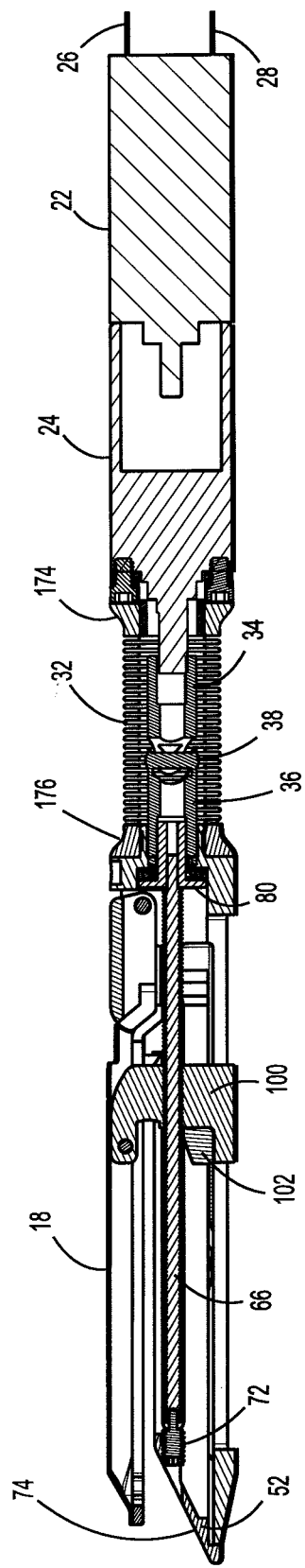
FIG. 5 is a side view, shown in section, of the remote motorized stapler head.

With reference to FIGS. 3 and 4, staple assembly 12 further includes a sled 60 which is provided to move anvil assembly 18 between the open and closed positions, as well as, drive staples 62 and 64 out of respective staple containing pockets 46 and 48 and into anvil plate 54 (FIG. 4). Sled 60 is mounted on a rotatable lead screw 66 extending through staple assembly 12. Lead screw 66 is rotatably supported at its distal end 68 by a pin 70 extending proximally from a threaded support 72. Threaded support 72 is threaded into a hole 74 formed in distal tip 52 of staple cartridge 14 (FIG. 4). Rotation of lead screw 66 causes sled 60 to move longitudinally within staple assembly 12.

Referring to FIG. 4, in order to rotate lead screw 66, and thus translate sled 60 through staple assembly 12, a proximal end 76 of lead screw 66 is connected to distal articulation shaft 36. Specifically, a keyed portion 78 of lead screw 66 engages a coupling 80. Coupling 80 includes a key shaft 82 which engages a keyhole 84 in distal articulation shaft 36. A flange 86 is positioned on key shaft 82 and includes a keyhole 88 for receipt of keyed portion 78 at proximal end 76 of lead screw 66. A thrust bearing 90 is provided to engage flange 86 and includes a hole 92 for passage of key shaft 82. Additionally, a washer 94 is provided between distal articulation shaft 36 and thrust bearing 90. Washer 94 also includes a hole 96 for passage of key shaft 82. As best shown in FIG. 4, motor 22 includes a motor shaft 98 for engagement with gearbox 24. As motor 22 is activated, rotation of motor shaft 98 causes rotation of gears (not shown) of gearbox 24 and thus rotation of drive shaft 40. Drive shaft 40 rotates proximal articulation shaft 34 and distal articulation shaft 36. Thus, rotation of distal articulation shaft 36 effects rotation of coupling 80 which in turn rotates lead screw 66 to translate sled 60 through staple assembly 12.

With reference to FIGS. 3 and 4, sled 90 generally includes a proximal sled member 100 and a distal sled member 102. Proximal sled member 100 is provided to move anvil assembly 18 between the open and closed positions as well as cut through staple tissue. Distal sled member 102 is provided to drive staples 62 and 64 from staple cartridge 44 and into anvil plate 54 to staple tissue captured therebetween. Proximal sled member 100 includes a transverse base 104 having a vertical leg 106 extending vertically from transverse base 104. A distally extending arm 108 extends distally from vertical leg 106. Vertical leg 106 includes a threaded bore 110 having a threaded inner surface 112 for receipt of lead screw 66. Rotation of lead screw 66 drives proximal sled member 100, and thus sled 90, distally and proximally within staple assembly 12. A distally facing cutting blade 114 is provided on vertical leg 106 intermediate threaded bore 110 and distally extending arm 108. As noted above, cutting blade 114 is provided to sever tissue as sled 90 moves distally within staple assembly 12.

A pinhole 116 is provided on a distal end 118 of arm 108. An anvil pin 120 is positioned within pinhole 116 and is provided to engage an anvil slot 122 formed in anvil plate 54 (FIG. 4). Movement of anvil pin 120 within anvil slot 122 moves anvil plate 54, and thus anvil assembly 18, between the open and closed positions. As noted hereinabove, anvil assembly 18 is pivotally mounted to staple cartridge 14. Anvil base 56 includes holes 124 and channel member 16 includes holes 126. A pin 128 extends through holes 126 and 124 to allow anvil base 56 to pivot relative to channel member 16. Anvil plate 54 includes a proximal portion 130, a tapered intermediate portion 132 and a longitudinally extending distal portion 134. Anvil slot 122 extends through proximal portion 130, tapered intermediate portion 132 and distally extending portion 134. Anvil slot 124 terminates in a transverse slot 136 such that when sled 60 reaches a distal most position, anvil pin 120 falls through transverse slot 136 allowing anvil assembly 18 to move to the open position. Anvil plate 54 is affixed to anvil base 56 by inserting proximal portion 130 into a distal end 138 of anvil base 56. Anvil cover 58 is affixed to anvil plate 54 by welding, gluing, or in snap fit fashion. Anvil cover 58 includes a pair of downwardly extending wings 140 provided that a proximal end 142 of anvil cover 58. Wings 140 prevent tissue positioned between anvil assembly 18 and staple cartridge 14 from being pinched as anvil assembly 18 is moved between the open and closed positions.

Referring now specifically to FIG. 4, distal sled member 102 includes a base 144 having vertically extending and tapered sides 146 and 148 extending vertically from base 144. Tapered sides 146 and 148 are provided to drive staples 62 with 64 into anvil plate 54 in a manner described in more detail hereinbelow. Base 144 distal sled member 102 is configured to be positioned about vertical leg 106 of proximal sled member 100. A stop 150 is provided on base 144 to engage vertical leg 106. A slot 152 for vertical leg 106 is provided on base 144 proximal of stop 150.

In order to drive staples 62 and 64 upwardly through staple pockets 46 and 48, staple cartridge 14 is provided with pushers 154 and 156 positioned between staples 62 and 64 respectively. As sled 60 moves distally relative to staple cartridge 14, tapered sides 146 and 148 of distal sled member 102 engage pushes 154 and 156 to drive staples 62 and 64 out of staple pockets 46 and 48 through tissue and into anvil plate 54. In order to secure staple cartridge 14 within channel member 16, staple cartridge 14 is provided with a pair of proximally extending legs 158 and 160 which are configured to extend into and engage a proximal portion 162 of channel member 16.

In order to connect proximal articulation shaft 34 and distal articulation shaft 36 of articulation section 30 between staple assembly 12 and motor assembly 20, a coupling 164 is affixed to gearbox 24 via a pair of threaded screws 166 and 168. Coupling 164 includes a throughbore 170 for receipt and support of proximal articulation shaft 34. A proximal end 172 of proximal articulation shaft 34 fits within throughbore 170. Articulation cover 32 is supported within articulation section 30 by a proximal support 174 and a distal support 176. Screws 178 and 180 secure proximal support 174 to articulation cover 32 while screws 182 and 184 secure distal support 176 to articulation cover 32. Proximal support 174 includes a throughbore 186 and distal support 176 includes a throughbore 188 for passage of respective proximal and distal articulation shafts 34 and 36. Articulation cover 32 includes a throughbore 190 for passage of the relative components. Articulation cover 32 further includes a flexible or corrugated outer surface 192 to allow articulation cover 32 to flex in various directions.

Figure 6:
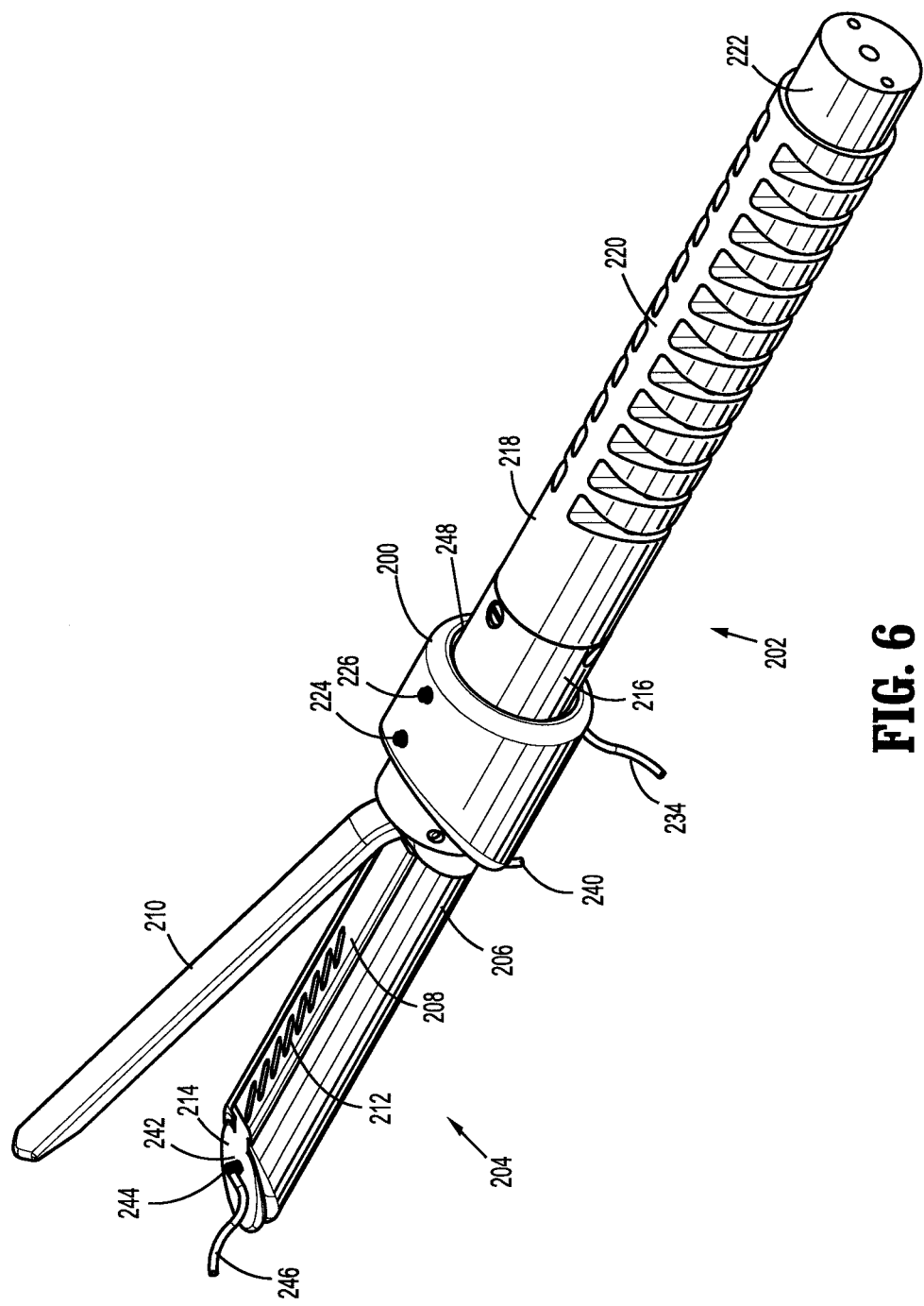
FIG. 6 is a perspective view of a remote motorized stapler head with an auxiliary collar.
Figure 7:
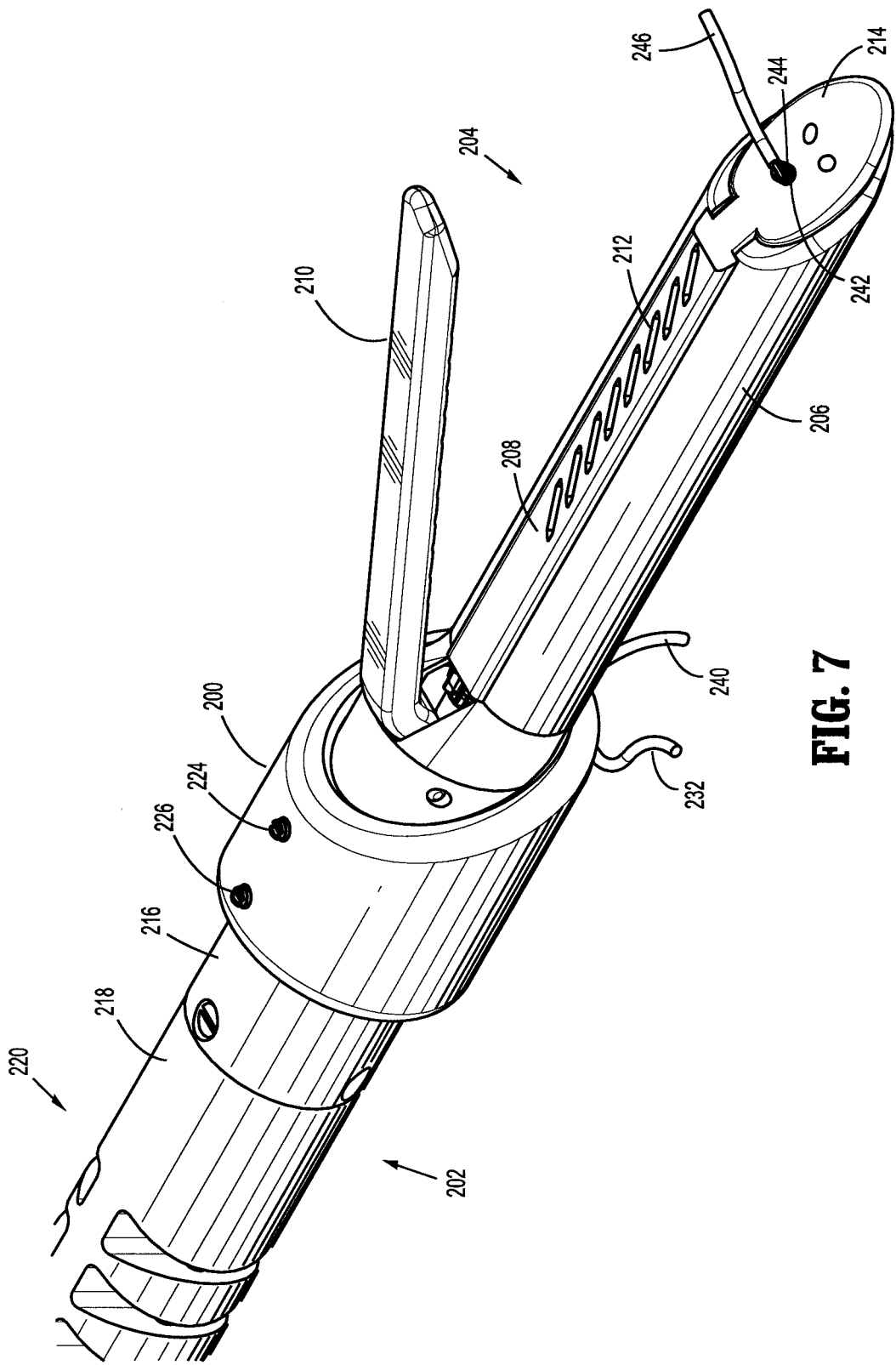
FIG. 7 is another perspective view of the remote motorized stapler head with the auxiliary collar.
Figure 8:
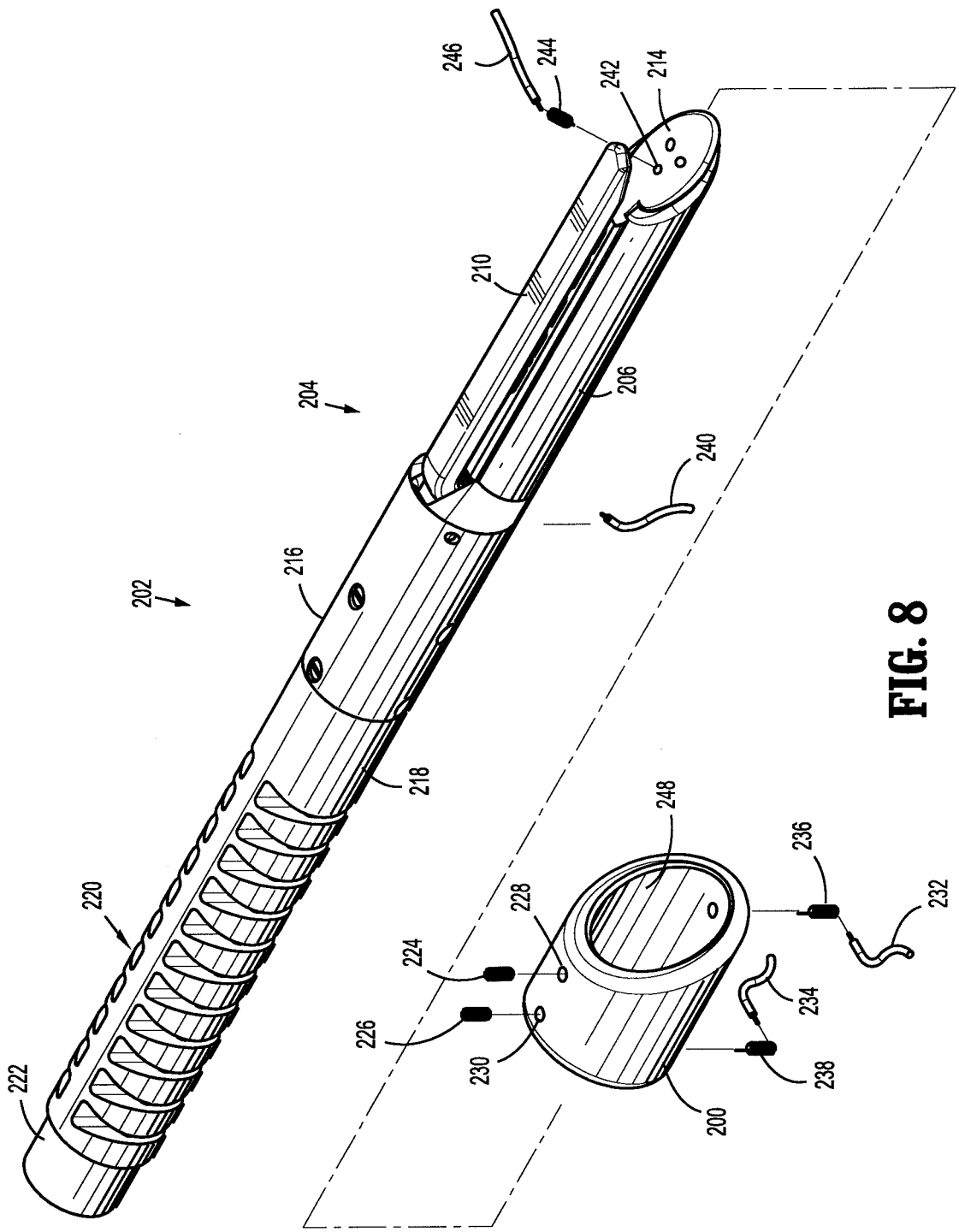
FIG. 8 is a perspective view similar to FIG. 7 with the auxiliary collar removed from the stapler head.

Referring now to FIGS. 6-8, there is disclosed an auxiliary collar 200 for use with a remotely actuated surgical stapler 202. Surgical stapler 202 is of the type having a staple assembly 204 including a channel member 206 supporting a staple cartridge 208. An anvil 210 is pivotally mounted to channel member 206. Staple cartridge 208 includes a plurality of staple pockets 212. Staple cartridge 208 further includes a tapered distal end 218 to facilitate manipulating staple assembly 204 about tissue. A proximal end 216 of channel member 206 is affixed to a distal end of a flexible gooseneck member 220 which allows staple assembly 204 to be manipulated about tissue. A proximal end 222 of gooseneck member 220 is connectable to an actuation structure, e.g., actuator 700 (FIG. 20), of surgical stapler 202. One embodiment of surgical stapler 202 is disclosed in U.S. patent application Ser. No. 12/244,797, filed Oct. 3, 2008, the entire contents of which are incorporated by reference herein.

Collar 200 may be used to act as a limit switch to determine the location of certain components within the surgical stapler 202. A pair of set screws 224 and 226 are provided to secure collar 200 about proximal end 216 of channel member 206. Set screws 224 and 226 extend through holes 228 and 230 in collar 200 and are tightened to engage proximal end 216 of channel member 206.

A pair of side wires 232 and 234 is provided to carry electrical signals to and from collar 200 to channel member 206. Side wires 232 and 234 are secured to collar 200 by screws 236 and 238. Screws 236 and 238 may be conductive or may have a non-conductive outer surface with a conductive interior to pass electrical signals directly to channel member 206. A center wire 240 may be provided and is directly attached to channel member 206.

Staple cartridge 208 may be provided with a threaded hole 242 formed in tapered distal end 214. A set screw 244 secures a wire 246 within hole 242. Wire 246 may function to carry electrical signals to and from tapered distal end 214.

Figure 9:
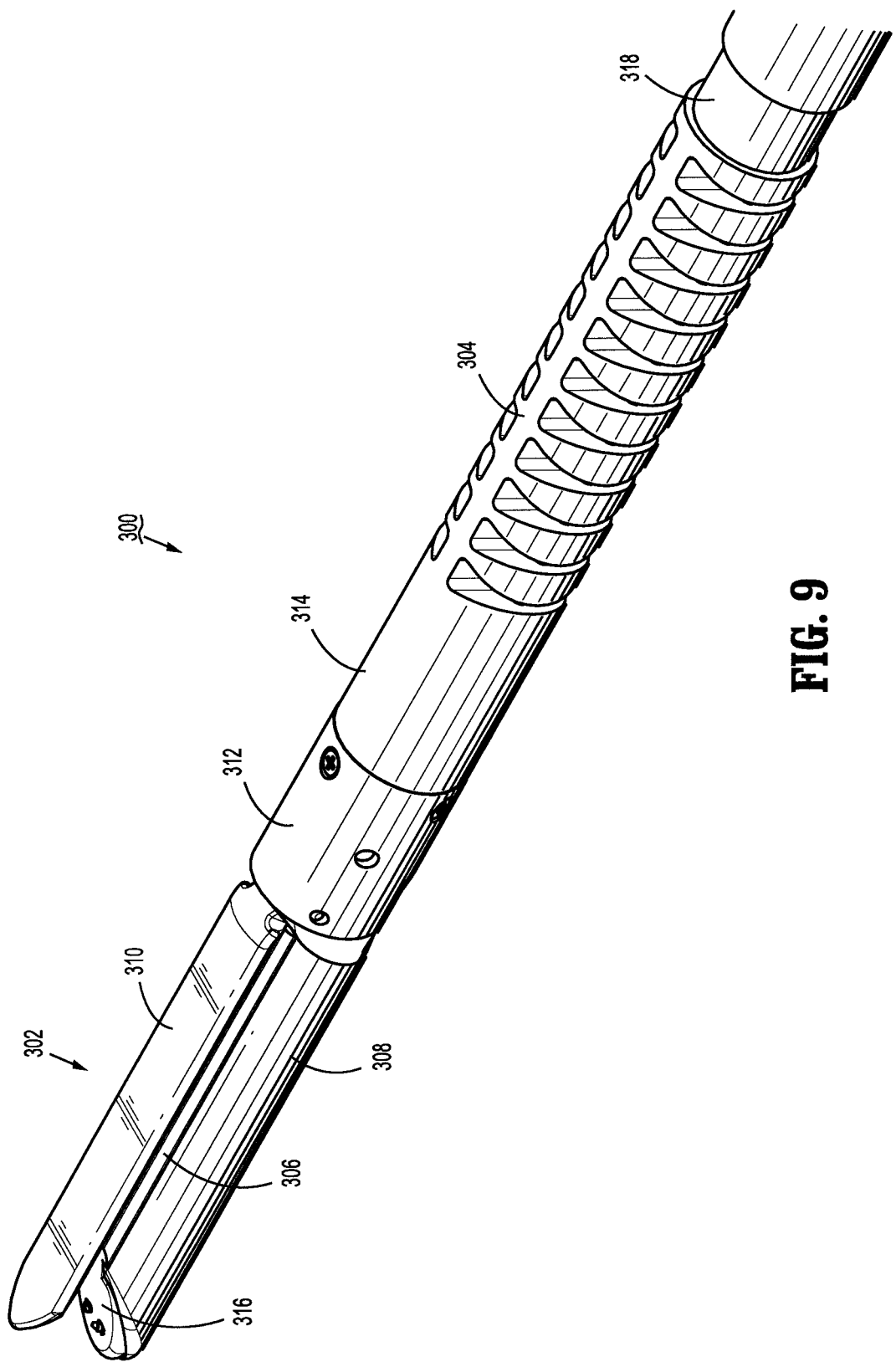
FIG. 9 is a perspective view of an alternative embodiment of a remote motorized stapler head.

Referring now to FIGS. 9-15, and initially with regard to FIG. 9, there is disclosed an alternative embodiment of a remote stapler head 300 for use with a surgical stapling apparatus, e.g., surgical stapler 202 (FIG. 7). Stapler head 300 generally includes a staple assembly 302 and a flexible gooseneck member 304 extending proximally from staple assembly 302. Staple assembly 302 includes a staple cartridge 304 and a channel member 302 for support of staple cartridge 304. An anvil 310 is pivotally mounted to channel member 302 and is movable from an open position spaced apart from staple cartridge 306 to a closed position adjacent staple cartridge 306. A proximal end 312 of channel member 308 is secured within a distal end 314 of gooseneck member 304. Staple cartridge 306 includes a tapered distal end 316 to facilitate manipulation of staple assembly 302 about tissue. A proximal end 318 is configured to be connected to remote actuating apparatus of surgical stapler 202 (FIG. 7).

Figure 10:
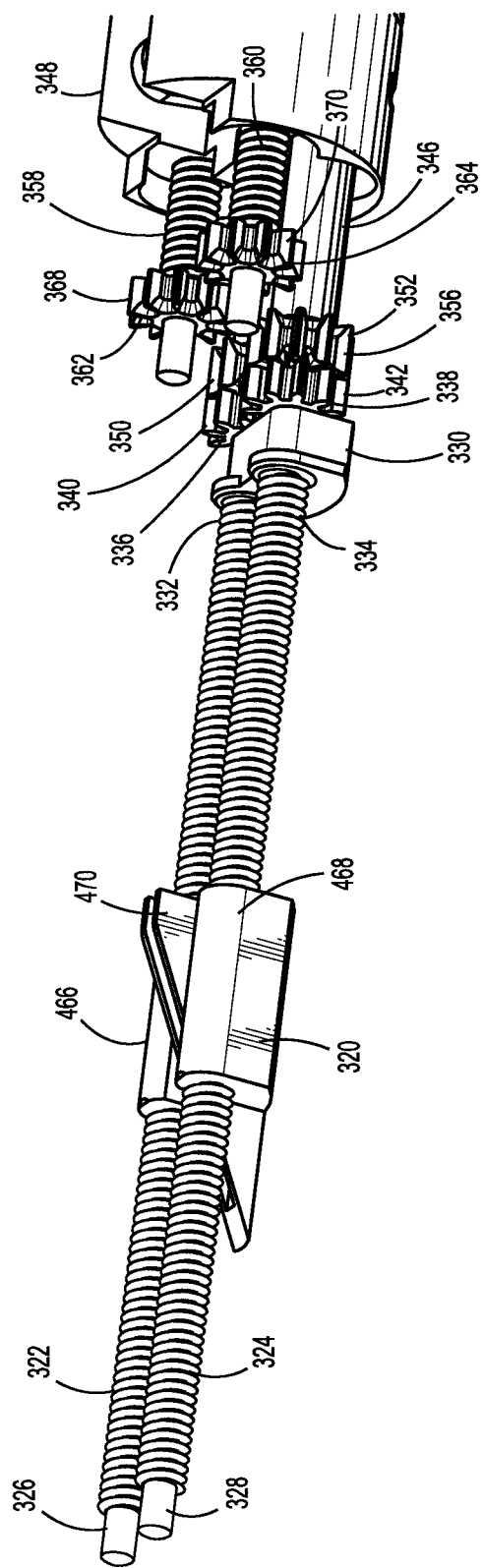
FIG. 10 is a perspective view of the remote motorized stapler head of FIG. 9 with staple assembly parts removed.
Figure 11:
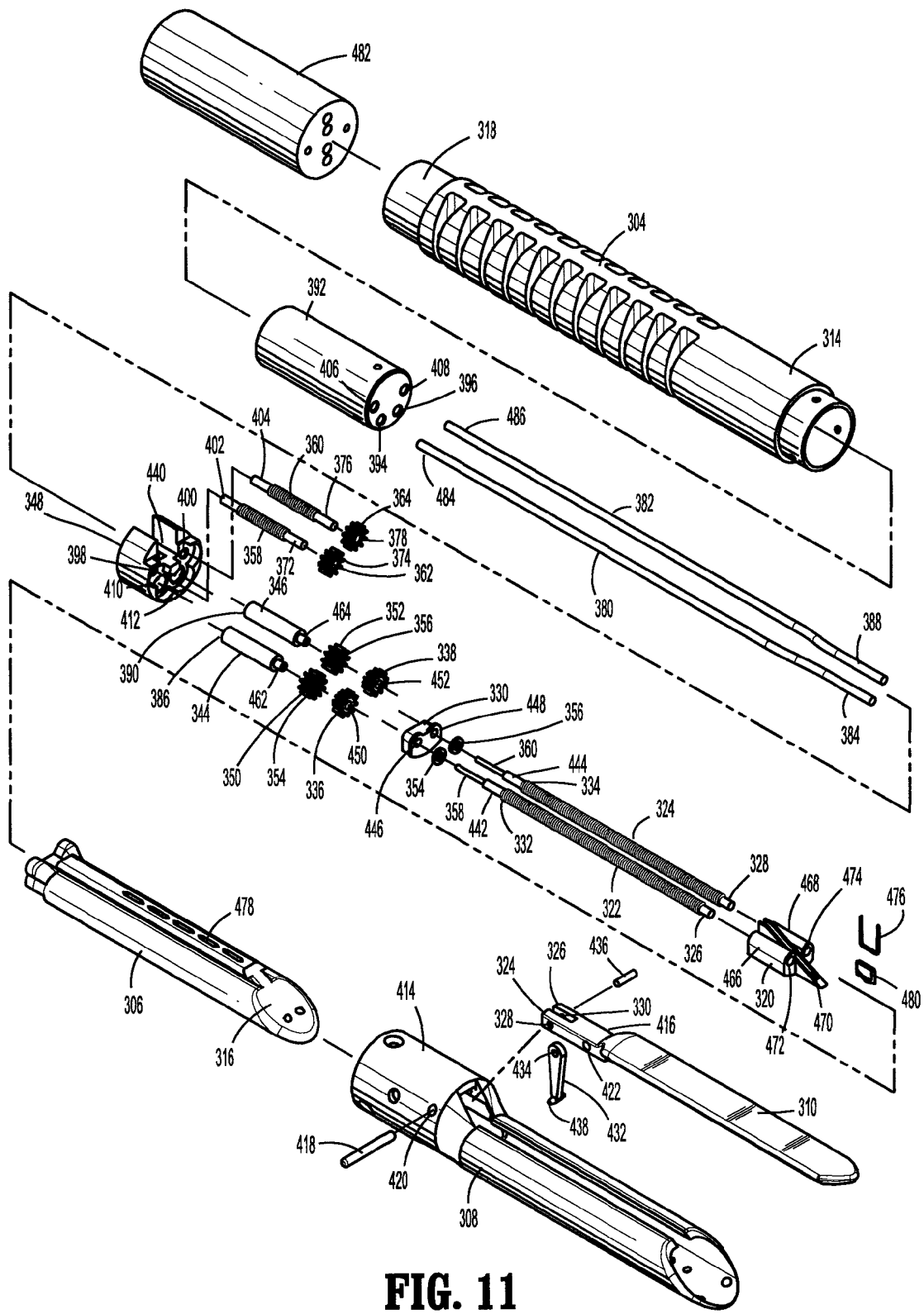
FIG. 11 is a perspective view, with parts separated, of the remote motorized stapler head of FIG. 9.

Referring to FIGS. 10 and 11, similar to the embodiment described hereinabove, remote stapler head 300 includes a sled 320 movably mounted upon first and second lead screws 322 and 324. Rotation of first and second lead screws 322 and 324 move sled 320 longitudinally within staple assembly 302 in a manner described hereinbelow. Smooth distal ends 326 and 328 are provided on first and second lead screws 322 and 324, respectively, to rotatably support first and second lead screws 322 and 324 within staple cartridge 304. A support block 330 is provided to rotatably support proximal ends 332 and 334 of first and second lead screws 322 and 324 respectively. A first pinion gear 336 is affixed to first lead screw 322 and a second pinion gear 338 is affixed to second lead screw 324. Rotation of first and second pinion gears 336 and 338 thus respectively rotate first and second lead screws 322 and 324. In order to ensure that first and second lead screws 322 and 324 rotate at a simultaneous, constant rate, first and second pinion gears 336 and 338 are provided with circumferential intermeshing teeth 340 and 342, respectively. Maintaining a constant and simultaneous rotation of first and second lead screws 322 and 324 insures that sled 320 will not cam or jam as it translates along first and second lead screws 322 and 324.

In order to rotate first and second lead screws 322 and 324, there is provided a first drive shaft 344 and a second drive shaft 346. First and second drive shafts 344 and 346 are mounted for longitudinal and rotary motion within a movable clamp cam 348. First drive shaft 344 includes a distally affixed first drive gear 350 and second drive shaft 346 includes a second distally affixed drive gear 352. First and second drive gears 350 and 352 are engageable with first and second pinion gears 336 and 338 to rotate first and second lead screws 322 and 324 in a manner described or detailed hereinbelow (see FIGS. 14 and 15).

First drive gear 350 includes teeth 354 and second drive gear 352 includes teeth 356. In order to move anvil 310 between the open and closed positions, remote staple had 300 includes a first short lead screw 358 and a second short lead screw 360. First and second short lead screws 358 and 360 are in threaded engagement with clamp cam 348. Rotation of first and second short lead screws 358 and 360 moves clamp cam 348 longitudinally within remote staple had 300. A first spaced pinion gear 362 is mounted on first short lead screw 358 and a second spaced pinion gear 364 is mounted on second short lead screw 360. First teeth 368 and second teeth 370 are affixed to first and second short lead screws 358 and 360, respectively. First and second teeth 368 and 370 engage teeth 354 and 356 on first and second drive gears 350 and 352 when first and second drive shafts 344 and 346 are in a proximal most position.

As best shown in FIG. 11, a first distal keyway 372 is provided on first short lead screw 358 and engages a first keyed bore 374 formed in first spaced pinion gear 362. Similarly, a second distal keyway 376 is provided on second short lead screw 360 and engages a second keyed bore 378 formed in second spaced pinion gear 362.

In order to rotate first and second drive shafts 344 and 346, and thus actuate staple assembly 302, remote staple head 300 includes first and second drive wires 380 and 382. Drive wires 380 and 382 all both rotatable and longitudinally movable through clamp cam 348. A distal end 384 of first drive wire 380 is affixed within a proximal end 386 of first drive shaft 344. A distal end 388 of second drive wire 382 is affixed within a proximal end 390 of second drive shaft 346. Thus, rotation of first and second drive wires 380 and 382 causes rotation of first and second drive shafts 344 and 346. Similarly, longitudinal movement of first and second drive wires 380 and 382 causes longitudinal movement of first and second drive shafts 344 and 346 through clamp cam 348.

Remote staple had 300 further includes a support tube 392. First and second drive wires 380 and 382 are longitudinally movable through wire boars 394 and 396, respectively of support tube 392. As noted hereinabove, first and second short lead screws 358 and 360 move clamp cam 348 longitudinally. Clamp cam 348 includes first and second threaded bores 398 and 400 for receipt of, and engagement with the first and second short lead screws 358 and 360. First and second ends 402 and 404 of first and second short lead screws 358 and 360 are rotatably supported within bores 406 and 408 of support tube 392. Clamp cam 348 additionally includes a pair of large bores 410 and 412 to allow clamp cam 348 to move along first and second drive shafts 344 and 346.

Clamp cam 348 is mounted for longitudinal movement within a proximal portion 414 of channel member 308. As noted hereinabove anvil 310 is pivotally mounted to channel member 308. Anvil 310 includes a proximal portion 416 configured to pivot around a pivot pin 418 in proximal portion 414 of channel member 308. Specifically, a pivot hole 420 is formed in channel member 308 for receipt of pivot pin 418. Likewise, a pivot hole 422 is provided in proximal portion 416 of channel member 308. Thus, anvil 310 is pivotally mounted to channel member 308. In order to move anvil 310 relative to channel member 308, proximal portion 416 of anvil 310 is provided with a pair of distally extending arms 424 and 426. Arms 424 and 426 are provided with cam holes 428 and 430. A cam 432 is provided to engage both anvil 310 and clamp cam 348. A cam hole 434 is provided in cam 432. A cam pin 436 extends through cam holes 428 and 430 in anvil 310 and through cam hole 434 in cam 432. A transverse bar 438 is provided on cam 432 and engages a pocket 440 formed in clamp cam 348. Longitudinal movement of clamp cam 348 within proximal portion 414 of channel member 308 moves cam 432 to pivot anvil 310 between the open and closed positions. (See also FIGS. 12 and 13).

In order to connect first and second lead screws 322 and 324 to first and second pinion gears 350 and 352, proximal portions 332 and 334 of first and second lead screws 322 and 324 are provided with keyways 442 and 444 which extends through bores 446 and 448 formed in support block 330 and engage first and second keyed bores 450 and 452 formed in first and second pinion gears 336 and 338. Washers 454 and 456 are provided to facilitate rotation of first and second lead screws 322 and 324. Proximal portions 332 and 334 of first and second lead screws 322 and 324 additionally include narrow diameter proximal ends 458 and 460 which extend into bores 462 and 464 formed in first and second drive shafts 344 and 346 (See also FIG. 15).

Sled 320 includes elongate sides 466 and 468. A tapered central portion 470 is provided intermediate sides 466 and 468. Sides 466 and 468 include respective threaded bores 472 and 474. Threaded bores 472 and 474 accept and engage first and second lead screws 322 and 324. As noted above, rotation of first and second lead screws 322 and 324 within bores 472 and 474 causes linear motion of sled 320 along first and second lead screws 322 and 324.

Figure 12:
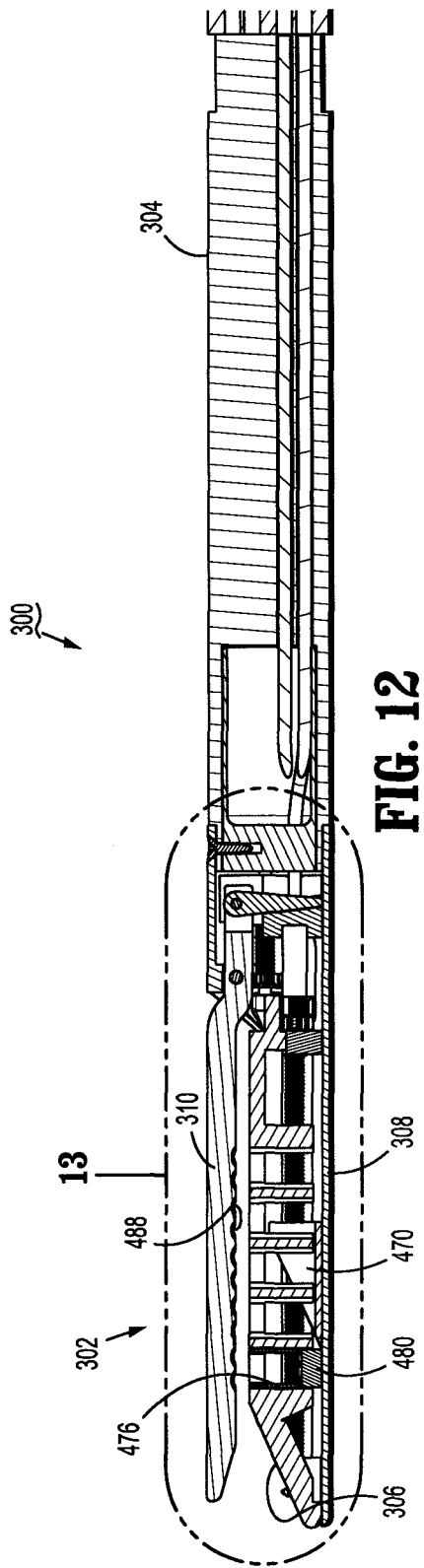
FIG. 12 is a side view, partially shown in section, of the remote motorized stapler head of FIG. 9.
Figure 13:
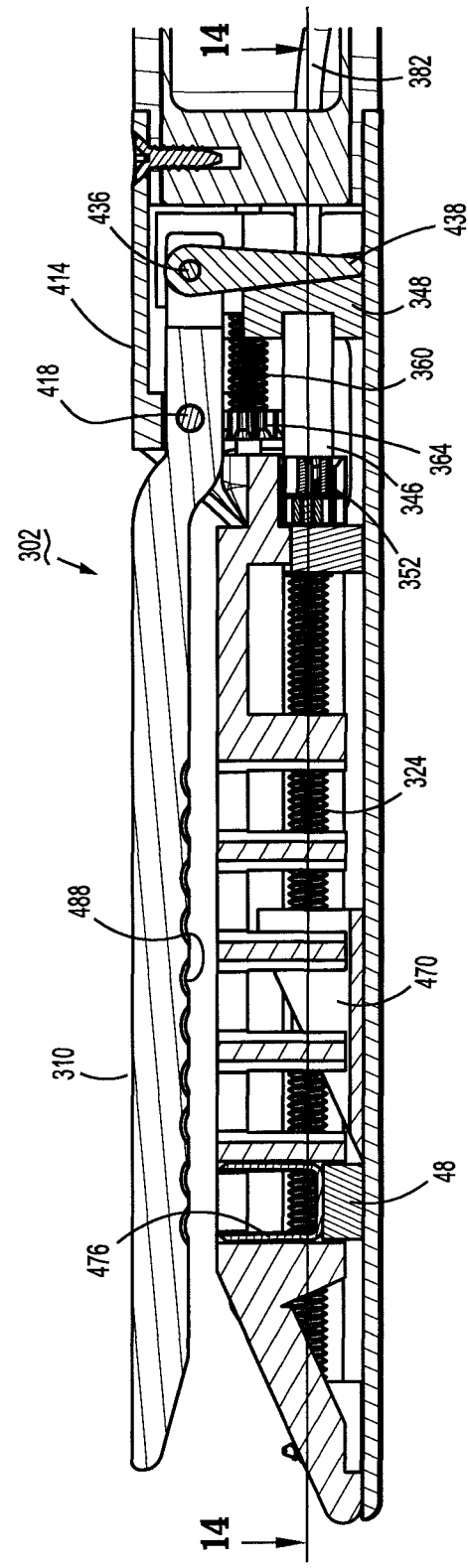
FIG. 13 is an enlarged area of detail view of FIG. 12.

With reference to FIGS. 11-13, tapered central portion 470 of sled 320 is provided to eject staples, such as staples 476, out of a row of staple pockets 478 provided in staple cartridge 306. Pushers 480 are located within staple pockets 478 and are interposed between staples 476 and tapered central portion 470.

A proximal actuator 482 is provided proximal to gooseneck portion 304 and engages proximal ends 484 and 486 of first and second drive wires 380 and 382 to both rotate and longitudinally move drive wires 380 and 382 in order to actuate staple assembly 302.

Figure 14:
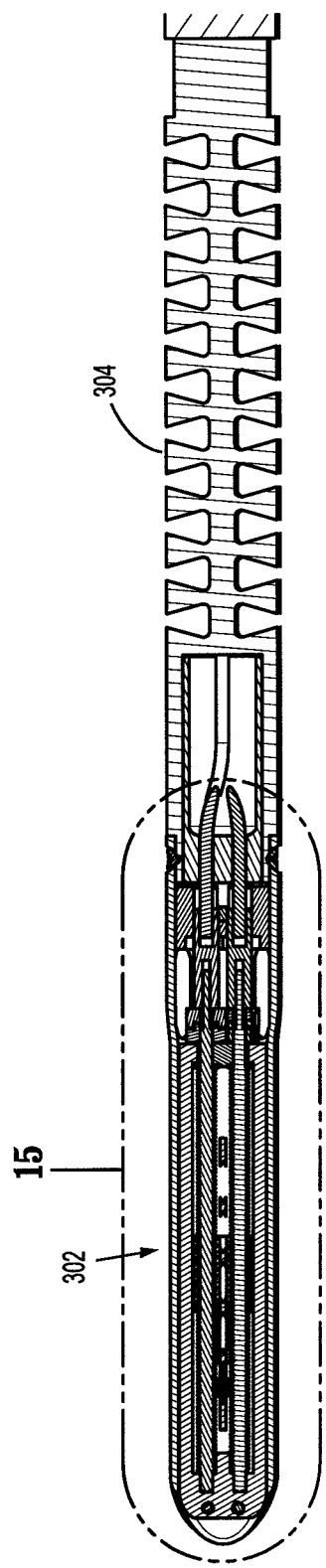
FIG. 14 is a sectional view taken along line 14-14 of FIG. 13.
Figure 15:
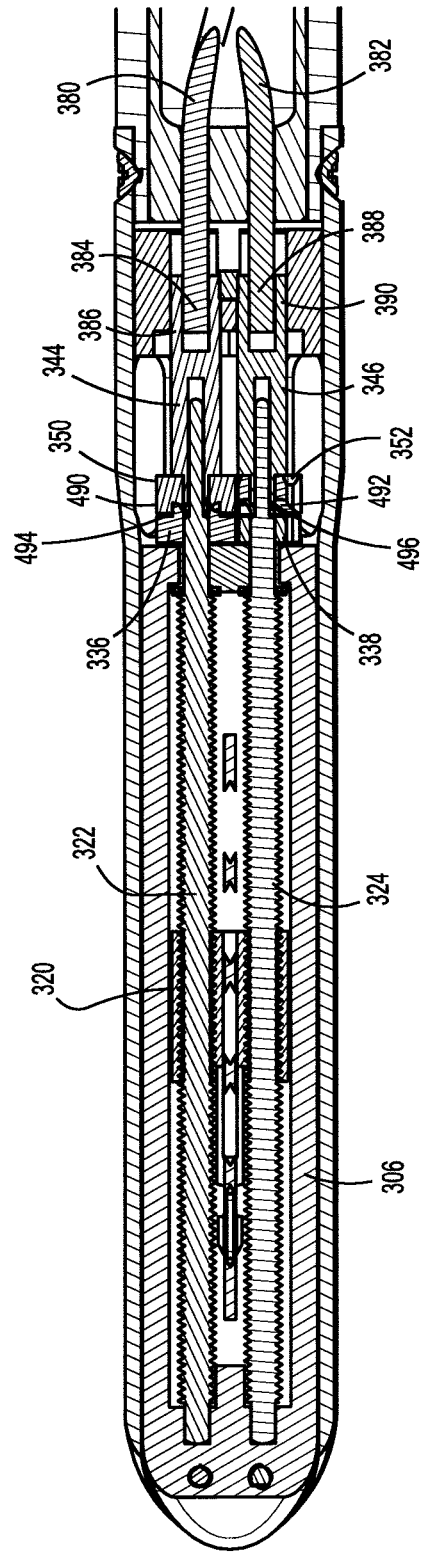
FIG. 15 is an enlarged area of detail view of FIG. 14.

With reference to FIGS. 14 and 15, and as noted herein above, first and second drive gears 350 and 352 on first and second drive shafts 344 and 346 engage first and second pinion gears 336 and 338 when first and second drive shafts 344 and 346 are moved to their distalmost position by first and second drive wires 380 and 382. Specifically, first and second drive gears 350 and 352 include respective distally facing teeth 490 and 492 which engage corresponding distally facing teeth 494 and 496 on first and second pinion gears 336 and 338. Thus, rotation of, for example, first drive wire 380 rotates first drive shaft 344 and first drive gear 350 which, in turn, rotates first pinion gear 336 and first lead screw 322 to cause sled 320 to move longitudinally within staple cartridge 306.

Figure 16:
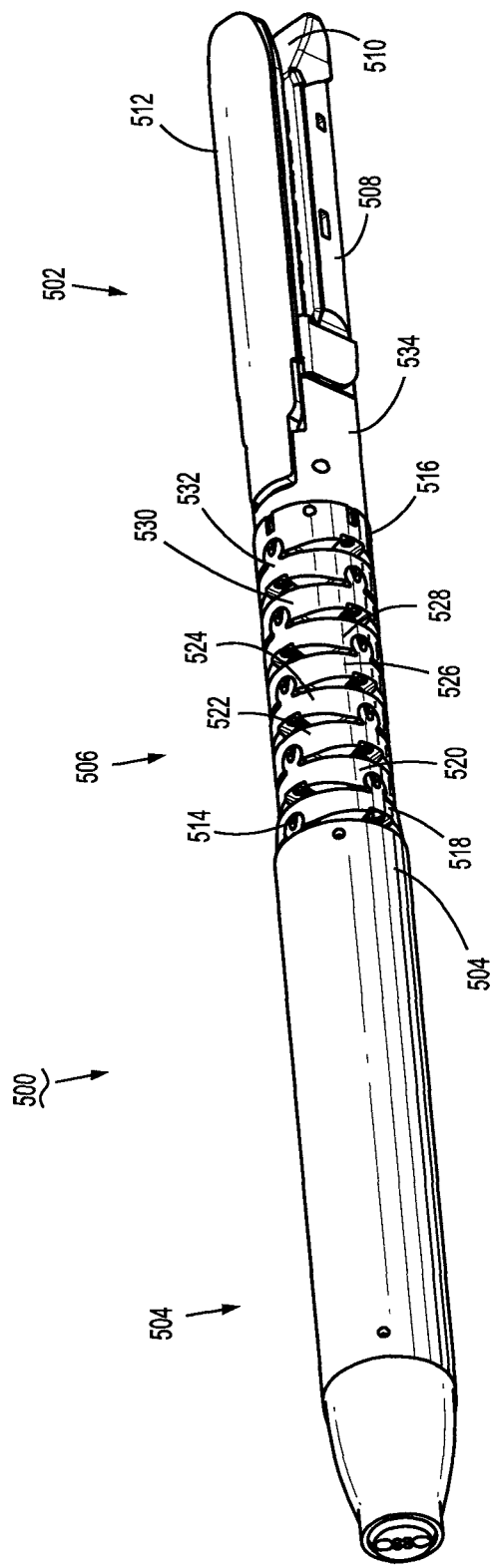
FIG. 16 is a perspective view of a further alternative embodiment of a remote motorized stapler head.
Figure 17:
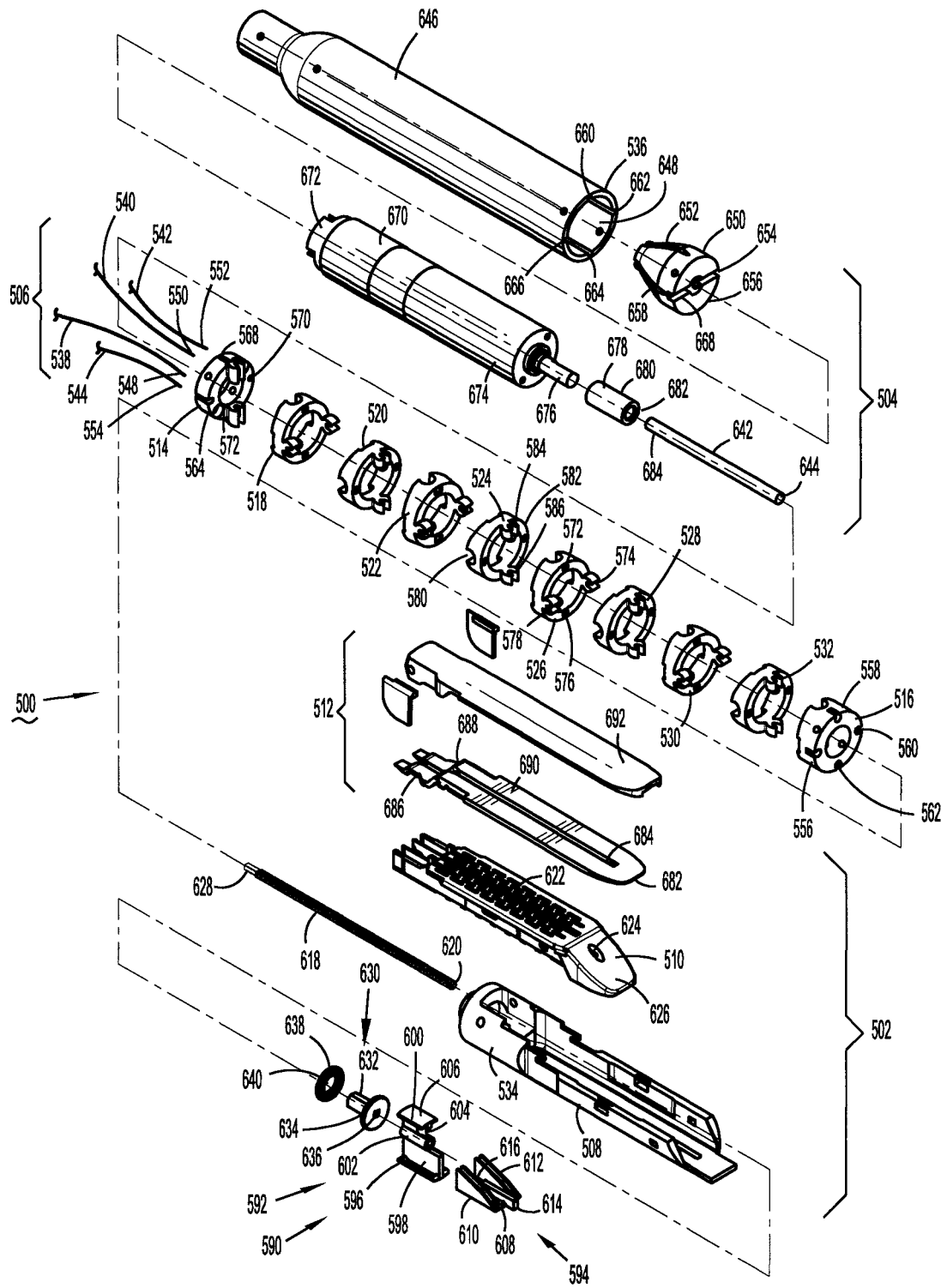
FIG. 17 is a perspective view, with parts separated, of the remote motorized stapler head of FIG. 16.

Referring now to FIGS. 16-19, and initially with respect to FIGS. 16 and 17, there is disclosed a further embodiment of a remote motor stapler head 500. Remote motor stapler head 500 generally includes a staple assembly 502 and a motor assembly 504. A flexible articulation assembly 506 is located intermediate staple assembly 502 and motor assembly 504. Similar to those embodiments described hereinabove, staple assembly 502 generally includes a channel member 508 having a staple cartridge 510 positioned therein. An anvil assembly 512 is pivotally mounted to channel member 508 and is movable from an open position spaced from staple cartridge 510 to closed position substantially adjacent staple cartridge 510.

Articulation assembly 506 is provided to allow staple assembly 502 to be moved both vertically and horizontally relative to motor assembly 504 in order to better position staple assembly 502 relative to tissue. Articulation assembly 506 includes a proximal link 514 and a distal link 560. A plurality of intermediate links such as, for example, intermediate links 518, 520, 522, 524, 526, 528, 530 and 532 are provided between proximal link 514 and distal link 516. Distal link 516 is affixed to a proximal portion 534 of channel member 598 and proximal link 514 is affixed to a distal end of motor assembly 504. Proximal link 514 along with intermediate links 520, 524, 528 and 532 allow staple assembly 502 to be moved horizontally relative to motor assembly 504. The remaining links 518, 522, 526 and 530 allow staple assembly 502 to be moved vertically relative to motor assembly 504.

Referring now to FIG. 17, in order to move articulation assembly 506 in the vertical and horizontal directions, remote motor staple head 500 includes plurality of control wires 538, 540, 544 and 546 which extend through articulation assembly 506 and terminate with distal link 516. Specifically, distal ends 548, 550, 552, and 554 of control wires 538, 540, 544 and 546, respectively, are anchored within respective notches 556, 558, 560 and 562 formed in distal link 516. (See distal ends 550 and 554 of control wires 540 and 544 in FIG. 19). Similarly, guide notches 564, 566, 568 and 570 are provided in distal link 514 to allow for passage of guide wires 540, 542, 544 and 548.

The structure of the intermediate links will now be described. The intermediate links are all identical with the exception of their orientation with respect to the immediately following and immediately preceding links. For example, with reference to intermediate link 526, each of the intermediate links includes four holes 572, 574, 576 and 578 oriented at 0°, 90°, 180° and 270° about the circumference of intermediate link 526. Holes 572, 574, 576 and 578 are provided for passage of control wires 538, 540, 544 and 546 respectively therethrough.

Likewise, with reference to intermediate link 524, each of the intermediate links includes a pair of proximally facing cut outs 580 and 582 and a pair of distally facing cups 584 and 586. The distally facing cups 584 and 586 of one intermediate link engage the proximally facing cut outs 580 and 582 of the next distally adjacent link. This allows adjacent links to pivot or articulate relative to each other. It should be noted that 572, 574, 576 and 578 of each of the links are oriented such that they pass through the cut outs and cups of that same link.

In order to move articulation assembly 506 opposed pairs of control wires for example control wires 540 and 544 are moved in opposite directions to exert a pushing and pulling force through the links. For example, when control wire 540 is retracted and control wire 544 is extended, proximal pressure is exerted on distal link 516 by control wire 540 and distal pressure is exerted on distal link 516 by control wire 544 causing articulation assembly 506 to pivot vertically upwardly. Similarly, for example, when control wire 542 is retracted and control wire 538 is advanced, proximal pressure is exerted on distal link 516 by control wire 542 and distal pressure is exerted on controlling 516 by control wire 538 closing articulation assembly 506 to pivot laterally in the horizontal direction.

The detailed components of staple assembly 502 will now be described. Similar to sled 60 described hereinabove with to respect remote motor staple head 10, remote motor staple head 500 including staple assembly 502 includes a longitudinally movable sled 590. Sled 590 includes a proximal sled member 592 and a distal sled member 594. Proximal sled member 592 includes a transverse base 596 and a lower vertical leg 598 extending upwardly from transverse base 596. Proximal sled member 592 additionally includes and upper vertical leg 600. A threaded throughbore 602 is provided intermediate lower vertical leg 598 and upper vertical leg 600. A transverse top 606 is provided on upper vertical leg 600 to move anvil assembly 512 between the open and closed positions in the manner described in more detail hereinbelow.

Distal sled member 594 includes a base 608 having tapered vertical side 610 and 612. Vertical side 610 and 612 are provided to eject staples 62, 64 (FIG. 4) from staple cartridge 510 into staple assembly 512. A stop 614 is provided on base 608 and a slot 616 is located in base 608 proximal of stop 614. Slot 616 is provided to accommodate lower vertical leg 598 of proximal sled member 592.

Similar to previous embodiments, remote motor staple head 300 is provided with a lead screw 618 which is configured to pass through and engage threaded throughbore 602 in sled 590. Rotation of lead screw 618 causes longitudinal motion of sled 590 through staple assembly 502. Lead screw 618 has a distal end 620. Like prior embodiments, staple cartridge 510 includes a plurality of staple containing pockets 622 which contain staples and pushers substantially similar to that described hereinabove. Distal end 620 of lead screw 618 is rotatably supported within a hole 624 provided in a tapered distal end 626 of staple cartridge 510. Lead screw 618 additionally includes a proximal end 628 which is configured to engage and be rotated by a coupling 630. Coupling 630 includes a proximal shaft 632 and a distal flange 634. A keyway 636 is provided in distal flange 634 for engaging keyed proximal end 628 of lead screw 618. A thrust bearing 638 is provided adjacent coupling 630 and includes a bearing hole 640 for passage of proximal shaft 632 of coupling 630.

Motor assembly 504 generally includes a housing 646 having a hollow interior 648. A guide member 650 is positioned within housing 646 and includes side slots 652, 654, 656 and 658 which function to guide control wires 538, 540, 544 and 546 initially into housing 646. Likewise, the interior of housing 646 is provided with four longitudinally extending housing slots 660, 662, 664 and 666 for guidance of the control wires. Guide member 650 additionally includes a cross slot 668. A motor 670 is provided within housing 646 and includes a proximal end 672 engageable with cross slot 668. Engagement of motor 670 with guide member 650 prevents rotation or canting of motor 670 within housing 646 during operation.

A gearbox 674 extends from motor 670 and includes a distally extending gear shaft 676. Gear shaft 676 is engaged with a proximal end 678 of a coupling 680. A distal end 682 of coupling 680 is fixedly engaged with a proximal end 684 of flexible drive shaft 642. Thus, actuation of motor 670 causes rotation of flexible drive shaft 642, located within articulation assembly 506, and thus rotation of lead screw 618.

Similar to those embodiments described hereinabove, anvil assembly 512 includes an anvil plate 682 having a longitudinally extending slot 684. Slot 684 accommodates the passage of upper vertical leg 600 of sled 590. Anvil plate 682 includes a proximal portion 686 which is configured to the fixedly engage channel member 508. Anvil plate 682 additionally includes an angled portion 688 and a distally extending longitudinal portion 690 extending from angled portion 688. In order to move anvil assembly from the open to the closed position, sled 590 is advanced distally such that transverse top 606 of sled 590 engages angled portion 686 to move anvil plate 682 from the open to the closed positions. As noted hereinabove, distal movement of sled 590 includes distal movement of distal sled member 594 causing tapered sidewalls 610 and 612 to eject staples from staple cartridge 508. Staple assembly 512 additional includes an anvil cover 692 which is affixed to anvil plate 682. A pair of side wings 694 and 696 is provided on anvil cover 692 to prevent pinching of tissue captured between anvil assembly 512 and staple cartridge 510.

As best shown in FIG. 18, control wires, such as, for example, control wires 540 and 544 pass into housing 646 and are initially guided therein by slots 652 and 656 in guide member 650. Thereafter control wires 540 and 544 pass alongside motor 670 and gearbox 674 and pass-through proximal link 514.

With reference to FIGS. 18 and 19, distal ends 550 and 554 of control wires 540 and 544 are secured within notches 558 and 562 in distal link 516. As best shown in FIG. 19, control wires 540 and 544 pass through holes in the intermediate links. For example, control wires 540 and 544 pass through holes 572 and 576 in intermediate link 526 as described in detail hereinabove. As shown, sled 590 rides along and is driven distally by lead screw 618 to both cam anvil assembly 512 to the closed position and eject staples 62, 64 (FIG. 4) into anvil assembly 512.

Figure 20:
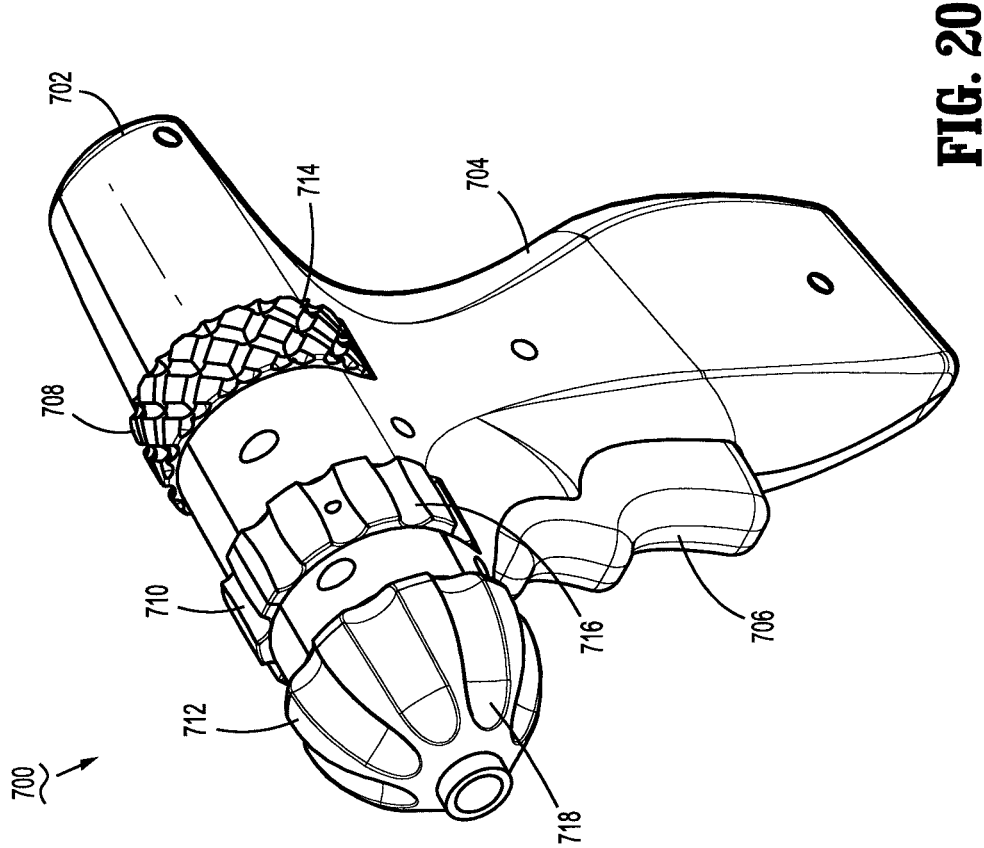
FIG. 20 is a perspective view of an actuator for use with the remote motorized stapler head of FIG. 16

Turning now to FIGS. 20-24, and initially with regard to FIG. 20, there is disclosed a control handle 700 for use with remote motor staple head 500 described hereinabove. Control handle 700 is configured to reciprocate pairs of control wires to affect articulation within remote motor staple head 500. While following description is given in contemplation of use with remote motor staple head 500, it will be understood that control handle 700 can be used to manipulate any surgical instrument requiring reciprocal movement of two separate pairs of control wires.

Control handle 700 generally includes a body portion 702 having a pistol grip portion 704 descending from body portion 702. A trigger 706 is provided on pistol grip portion 704 to remotely actuate a motor provided in the surgical instrument control by control handle 700. Control handle 700 further includes a first control knob 708, a second control knob 710 and a third control knob 712. First control knob 708 is provided to reciprocate a first pair of control wires and second control knob 710 is provided to reciprocate a second pair of control wires. Third control knob 712 is provided to reciprocate both pairs of control wires simultaneously.

In order to provide tactile differentiation between the various control knobs, first control knob 708 includes a cross-hatched surface 714, second control knob 710 includes a ribbed surface 716 and third control knob 712 includes a fluted surface 718.

Figure 21:
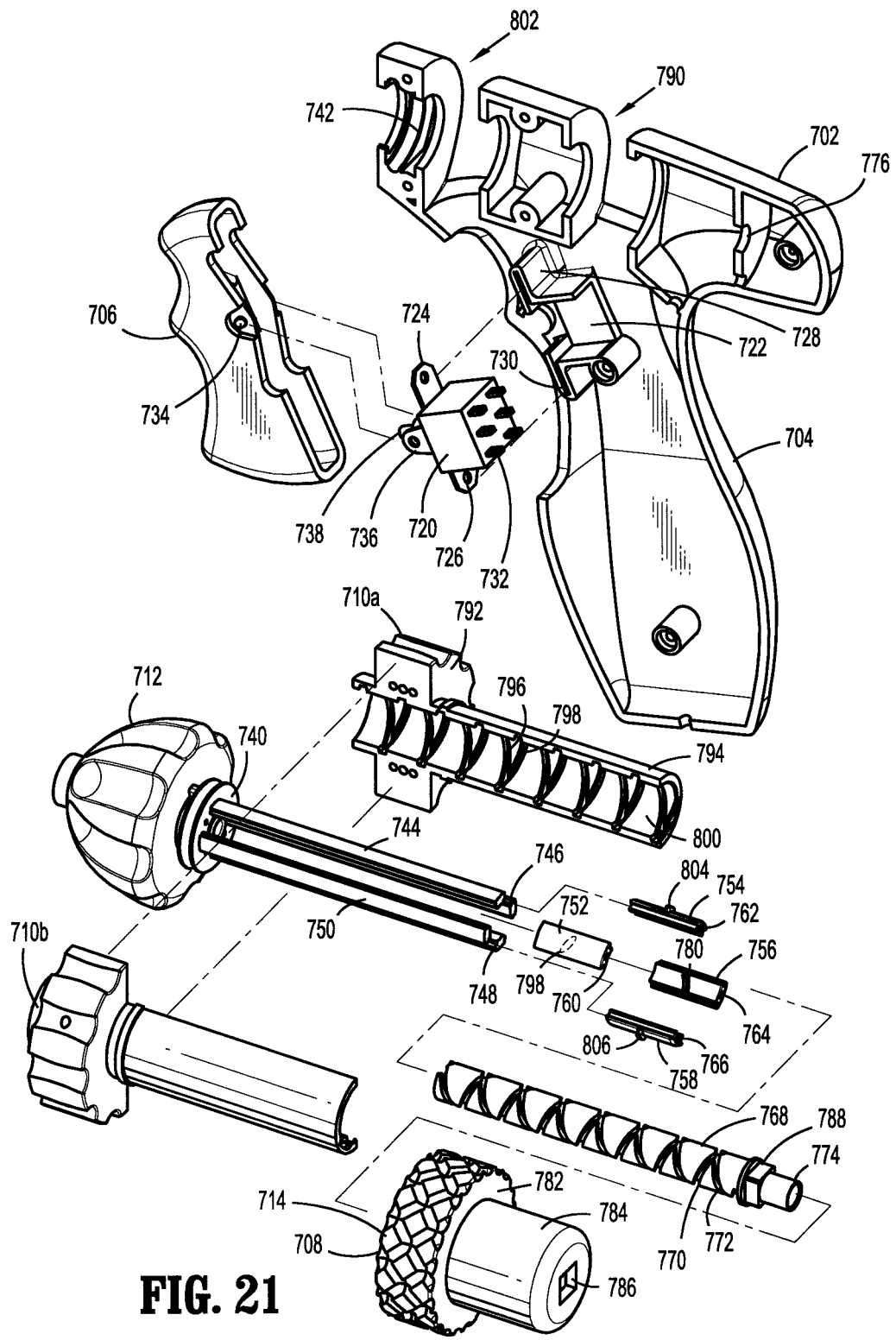
FIG. 21 is a perspective view, with parts separated, of the actuator.

Referring now to FIG. 21, control handle 700 is illustrated, with parts separated, and half of body portion 702 and pistol grip portion 704 removed. As noted hereinabove, trigger 706 is provided to actuate a remotely positioned motor. An electrical switch 720 is provided in a pocket 722 formed within pistol grip portion 704. Tabs 724 and 726 on electrical switch 720 engage slots 728 and 730 formed in pocket 722 to secure electrical switch 720 within pistol grip portion 704. Electrical switch 720 is provided with one or more electrical contacts 732 which are configured to receive wires running to the remote motor of the surgical instrument. While not specifically shown, provisions for a power source may also be provided within pistol grip portion 704. Trigger 706 includes a pin 734 which is mounted within a bracket 736 on electrical switch 720 to pivotally mount trigger 706 on pistol grip portion 704.

As noted hereinabove, third control knob 712 is rotatably mounted to body portion 702. Third control knob 712 includes a collar 740 which is rotatably mounted within a journal 742 formed in body portion 702. A plurality of slide guides 744, 746, 748 and 750 extend proximally from collar 740 through body portion 702. In order to reciprocate two pairs of control wires, control handle 700 is provided with slides 752, 754, 756 and 758. Opposed pairs of the slides are designed to reciprocate longitudinally within the spaces provided between the slide guides. For example, slides 752 and 756 move in opposite directions within the spaces defined between respective pairs of slide guides 744 and 750 and 746 and 748. Likewise, slide 754 and 758 move in opposite directions between the spaces defined between respective pairs of slide guides 744 and 746 and 748 and 750.

Distal ends of control wires (not shown) are secured within the holes 760, 762, 764 and 766 formed within slides 752, 754, 756 and 758 respectively. Thus, opposing movement of slides 752 and 756 function to reciprocate a first pair of control wires while opposing movement of slides 754 and 758 reciprocate a second pair of control wires.

In order to reciprocate slides 752 and 756 within housing 702, a dual grooved shaft 768 is rotatably supported within housing 702. Shaft 768 includes a first helical groove 770 formed in shaft 768 and spiraling in a first direction and a second helical groove 772 formed in shaft 768 and spiraling in a second direction opposite the first direction. A smooth proximal end 774 of shaft 768 is rotatably supported within a collar 776 formed in body portion 702. Slide 752 includes an interior tab 778 (FIG. 24) and slide 756 includes an interior tab 780. Interior tabs 778 and 780 ride within first and second helical grooves 770 and 772 respectively. Thus, rotation of shaft 768 within body portion 702 reciprocally moves one of slides 752 and 756 distally and simultaneously moves the other of slides 752 and 756 proximally to reciprocate the control wires connected to slides 752 and 756.

Figure 22:
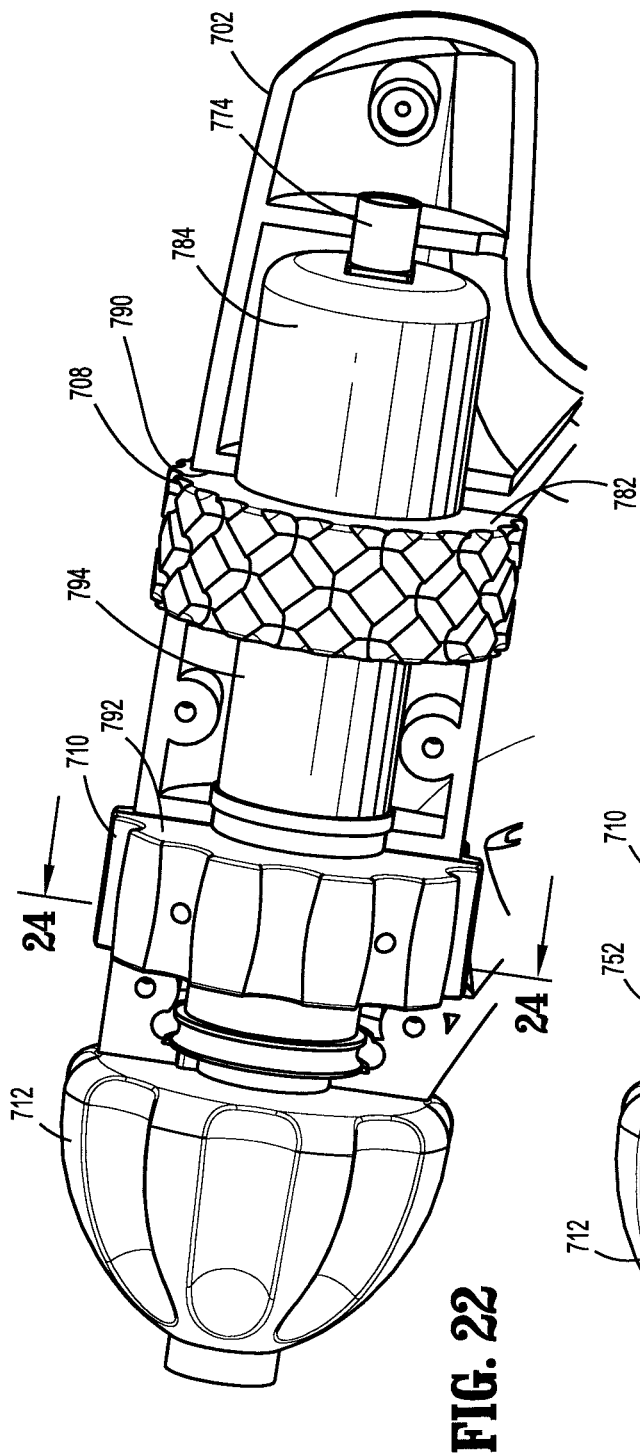
FIG. 22 is a side perspective view of the actuator with half of a handle housing removed.

First control knob 708 is provided to rotate shaft 768 within body portion 702. First control knob 708 includes a flange portion 782, incorporating crosshatched surface 714, and a proximally extending shaft 784. Shaft 784 includes a keyway 786. Shaft 768 extends between slide guides 744, 746, 748 and 750 and through third control knob 712. A key 788 formed on shaft 768 is secured within keyway 786 in third control knob 712. First control knob 708 is rotatably supported within an opening 790 formed in body portion 702 (FIG. 22). Thus, rotation of first control knob 708 causes reciprocal longitudinal motion of slides 752 and 756 within body portion 702 to reciprocate a pair of control wires.

Second control knob 710 is provided to move slides 754 and 758 longitudinally within body portion 702. Second control knob 710 is provided as to halves 710a and 710b. The following discussion will be made with regard to second control knob half 710a. However, it will be understood that both halves are structurally and functionally identical. Second control knob 710 includes a flange 792, incorporating ribbed surface 716, and a proximally extending shaft 794. First and second helical grooves 796 and 798 are formed in an inner surface 800 of second control knob 710. First and second helical grooves 796 and 798 spiral in opposite directions. Second control knob 710 is supported within a space 802 formed in body portion 702 (FIG. 22). Slides 754 and 758 are provided with tabs 804 and 806 respectively. Tabs 804 and 806 ride within first and second helical grooves 796 and 798 formed in second control knob 710. Thus, rotation of second control knob 710 causes reciprocal motion of slides 754 and 758 within body portion 702 to cause reciprocal motion of the respective attached control wires.

Figure 23:
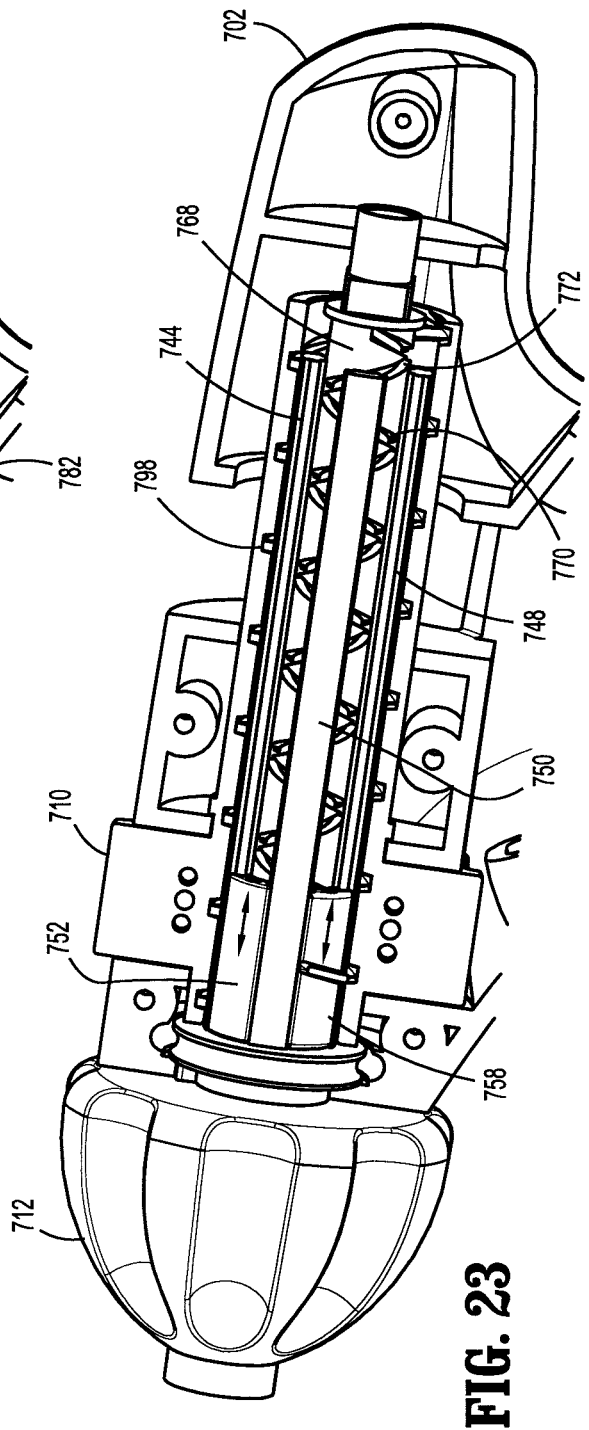
FIG. 23 is a side perspective view of the actuator with half the handle housing and control knobs removed.
Figure 24:
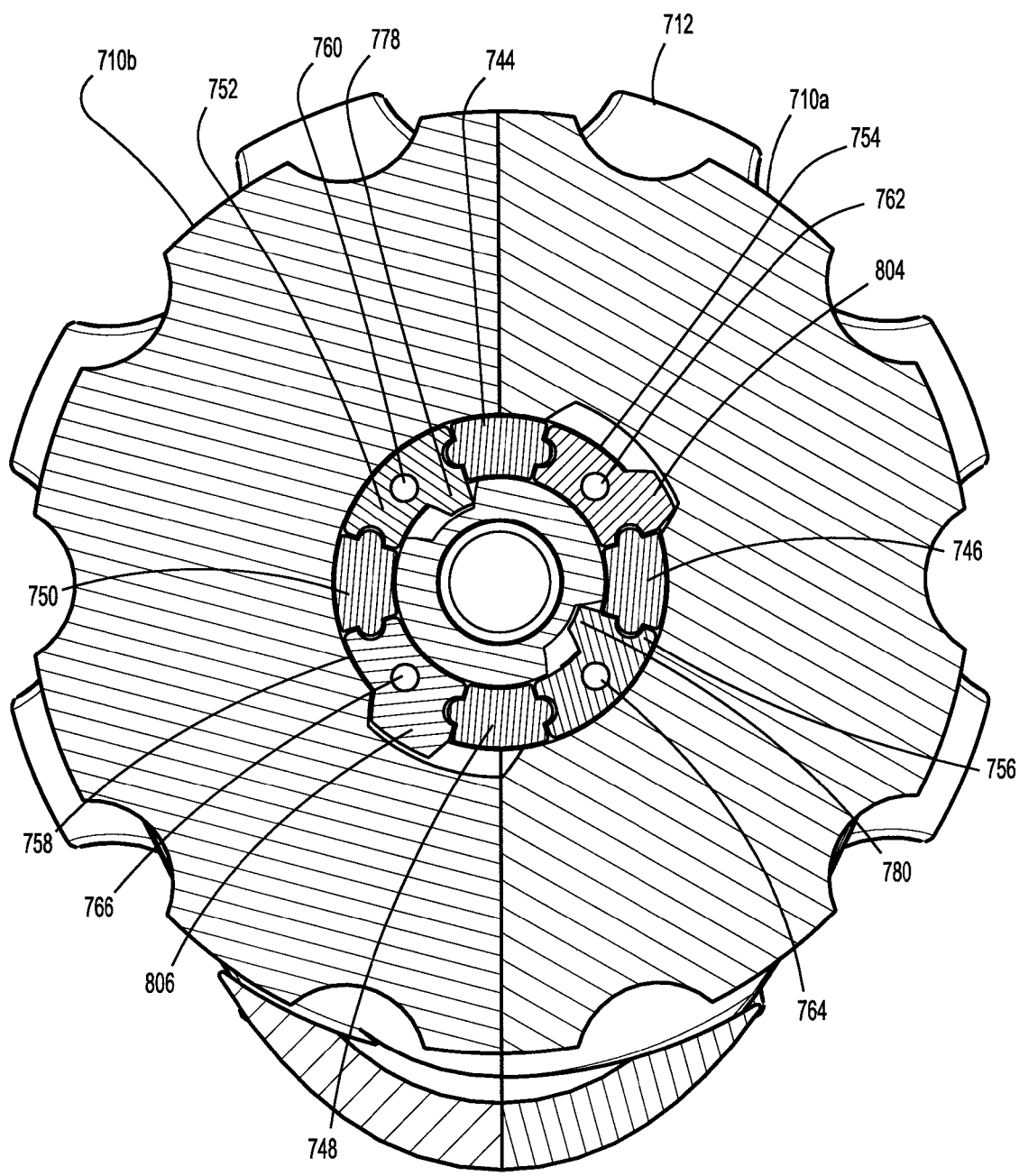
FIG. 24 is an end view taken along line 24-24 of FIG. 22.

Referring now to FIGS. 21, 23 and 24, rotating third control knob 712 causes rotation of slide guides 744, 746, 748 and 750 within body portion 702. With first control knob 708, and thus shaft 768, remaining stationary and second control knob 710 remaining stationary, the rotation of the slide guides forces slides 752, 754, 756 and 758, and specifically tabs 778, 780, 804 and 806 respectively, to move within their associated respective helical grooves such that slides 752, 754, 756 and 758 all simultaneously reciprocate within body portion 702 to reciprocate their attached control wires. Thus, rotation of third control knob 712 effects articulation of the associated articulation section into separate directions simultaneously.

Figure 25:
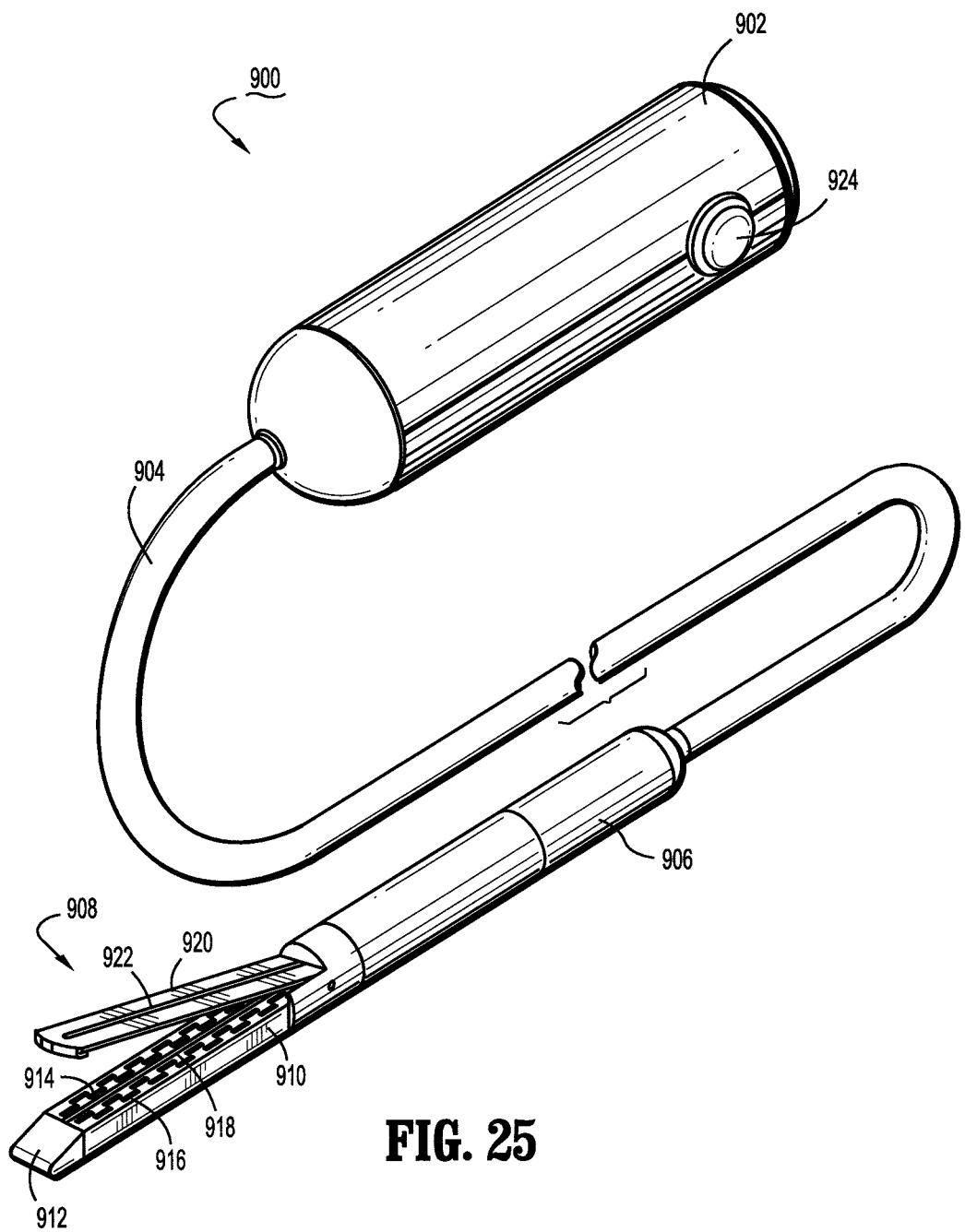
FIG. 25 is a perspective view of a further embodiment of a surgical stapler with a motor in the stapler head.

Referring now to FIGS. 25-33, and initially with regard to FIG. 25, there is disclosed a further alternative embodiment of a flexible, remote motorhead surgical stapler 900 for use in surgical procedures. Surgical stapler 900 generally includes a handle 902 having a highly flexible, elongate member 904 extending from handle 902. Elongate member 904 is of a highly flexible and pliable nature and may consist of thin control wires surrounded by a protective sheath (not shown). A housing 906 extends from elongate member 904 and includes a staple assembly 908. As with prior embodiments, staple assembly 908 generally includes a channel member 910 containing a staple cartridge 912. Staple cartridge 912 includes rows of staple containing pockets 914 and 916 as will be described in more detail hereinbelow. A knife slot 918 is provided in staple cartridge 912 between rows of staple pockets 914 and 916. An anvil 920 is pivotally attached to channel member 910 and is movable from an open position spaced apart from staple cartridge 912 to a closed position substantially adjacent staple cartridge 912. Anvil 920 includes an anvil slot 922 to facilitate moving anvil 920 between the open and closed positions. A control button 924 is provided on handle 902 to actuate staple assembly 908.

Figure 26:
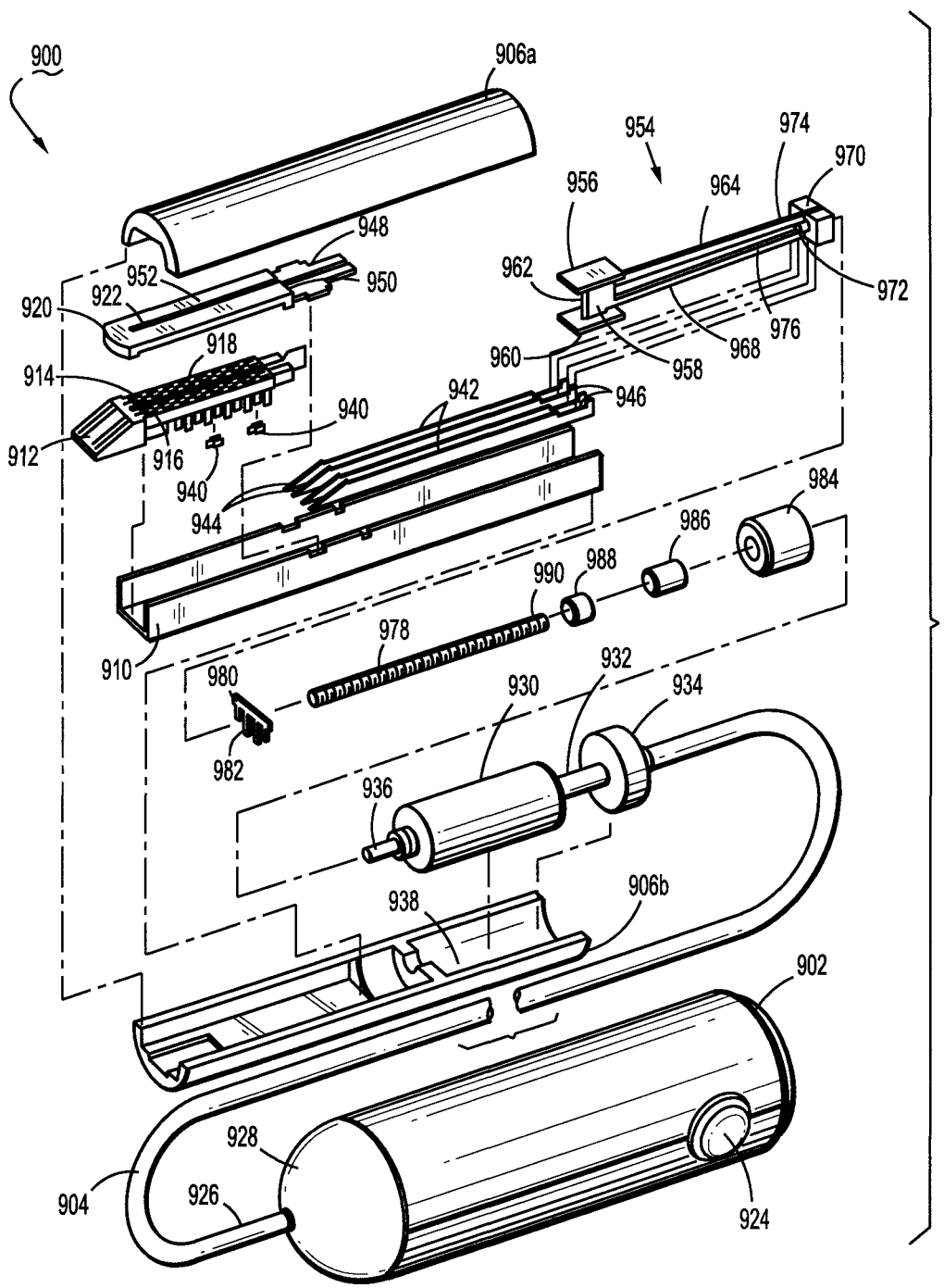
FIG. 26 is a perspective view, with parts separated, of the surgical stapler of FIG. 25.

With reference to FIG. 26, a proximal end 926 of elongate member 904 extends from a distal end 928 of handle 902. A motor assembly 930 is provided at a distal end 932 of elongate member 904. Motor assembly 930 may consist of a motor, gearbox and power source. Alternatively motor assembly 930 may consist of a motor and gearbox or simply a motor alone. A gasket 934 is provided about distal end 932 of elongate member 904 to seal motor assembly 930 within housing 906. A keyed drive shaft 936 extends from motor assembly 930. Motor assembly 930 is located within a proximal portion 938 of housing 906.

As noted hereinabove, staple assembly 908 includes a staple cartridge 912 containing a plurality of staples 62, 64 (FIG. 4) contained within staple pockets 914 and 916. A plurality of pushers 940 are positioned within staple pockets 914 and 916 to facilitate ejecting staples out of staple cartridge 912 and into anvil 920. In order to eject staples out of staple cartridge 912, a plurality of camming bars 942 are provided within staple assembly 908. Camming bars 942 include distal camming surfaces 944 configured to engage pushers 940. Camming bars 942 further include proximal engagement notches 946.

Anvil 920 includes a proximal portion 948 which is affixed to channel member 910. And will 920 further includes an angled portion 950 extending distally from proximal portion 948 and a longitudinal distal portion 952 extending distally from angled portion 950. Angled portion 950 provides a camming surface to move anvil 920 between the open and closed positions. As shown, anvil slot 922 extends through proximal portion 948, angled portion 950 and substantially the length of longitudinal distal portion 952.

In order to move camming bars 942 within staple assembly 908, there is provided a camming beam 954. Camming beam 954 includes an upper beam portion 956, a central web portion 958 and a lower beam portion 960. Upper beam portion 956 is substantially planer and engages angled portion 950 of anvil 920 to move anvil 920 between the opening closed positions. As upper beam portion 956 engages angled portion 950, central web portion 958 of camming beam 954 passes through anvil slot 922. A cutting blade 962 is provided on lower beam portion 960 to sever stapled tissue. Upper and lower beam extensions 964 and 968, respectively, extend proximally from central web portion 958. A drive member 970, having a threaded bore 972, is provided at proximal ends 974 and 976 of upper and lower beam extensions 964 and 968, respectively. Drive member 970 is configured to reside within proximal engagement notches 946 in camming bars 942. Distal movement of drive member 970 moves camming bars 942 distally to drive staples out of staple pockets 914 and 916 and into anvil 920. Additionally, distal movement of drive member 970 advances camming bar 954 causing upper beam portion 956 to cam anvil 920 to the closed position and advance cutting blade 962 to sever stapled tissue.

In order to connect motor assembly 930 to camming beam 954, there is provided a drive or lead screw 978. A support gate 980 is mounted within channel member 910 and includes a hole 982 for passage of lead screw 978. Lead screw 978 is driven by a motor assembly 930 and is connected to keyed drive shaft 936 of motor assembly 930 by an outer support hub 984, an intermediate support hub 986 and an inner engagement hub 988. Inner engagement hub 988 is fastened to proximal end 990 of lead screw 978 and is engaged within intermediate support hub 986. Intermediate support hub 986 is coaxially disposed within outer support hub 984. It should be noted that a portion of channel member 910 along with outer support hub 984, intermediate support hub 986 and inner engagement hub 988 are disposed within a distal portion 992 of housing 938.

Figure 27:
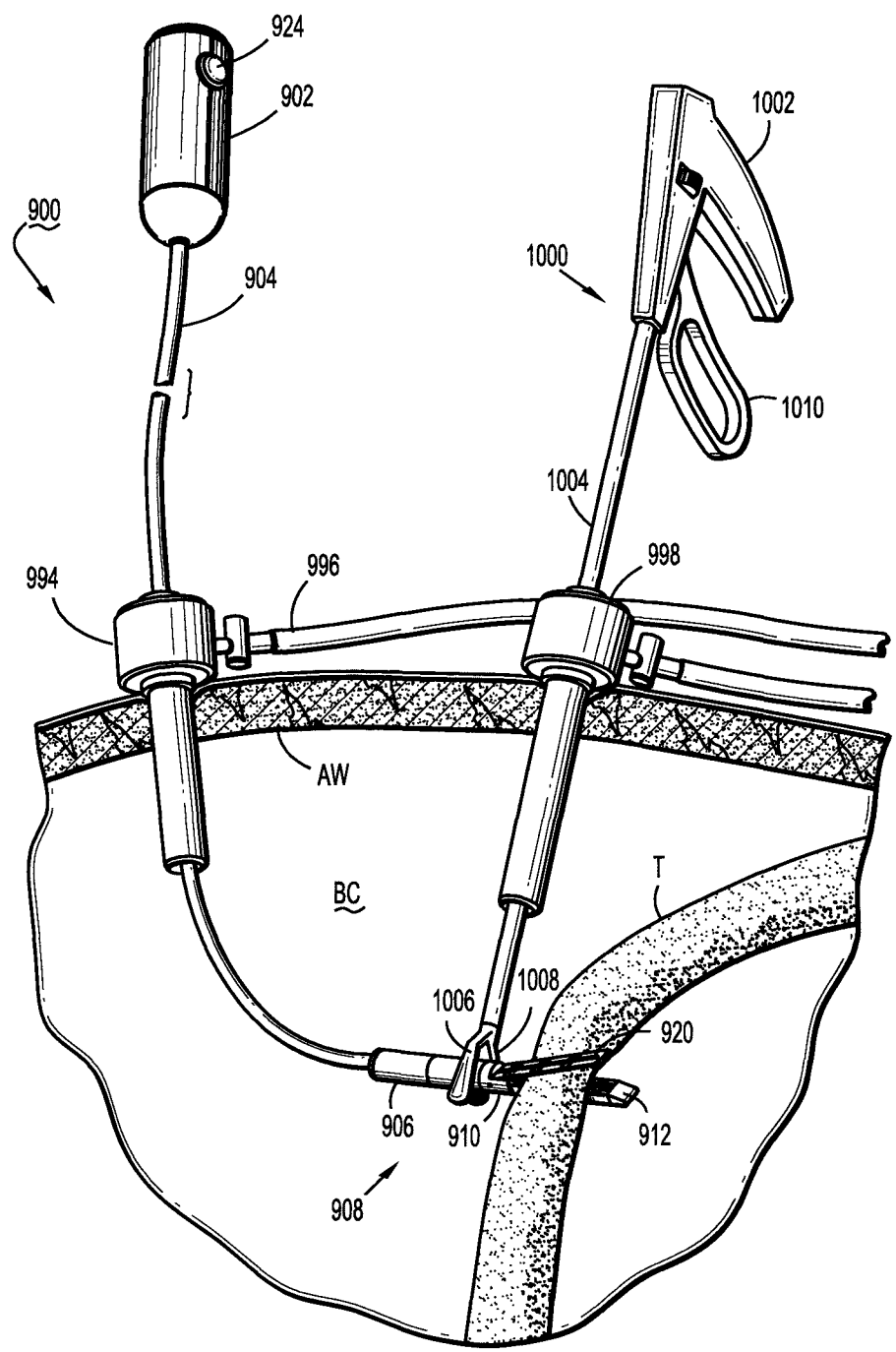
FIG. 27 is a perspective view, partially shown in section, of the surgical stapler of FIG. 25 in use within a body cavity.

Referring now to FIGS. 27-33, and initially with regard to FIG. 27, the use of surgical stapler 900 to remotely stapled tissue will now be described. Initially, an incision is made through the abdominal wall AW of a patient and a first port 994 is inserted therethrough. First port 994 is hollow and includes a source of insufflation fluid 996 for creating an operative space within a body cavity BC. Surgical stapler 900 is manipulated so as to "drop" housing 906, including staple assembly 908, through first port 994. As noted hereinabove, elongate member 904 is extremely flexible allowing housing 906 and staple assembly 908 to be easily positioned relative to a tissue T to be operated upon. Advantageously, handle 902, including control button 924, remains outside of abdominal wall AW and, being connected to elongate member 904, can easily be manipulated by the surgeon. Housing 906, including staple assembly 908, may be manipulated by hand relative to tissue T.

Alternatively, a second incision may be made through abdominal wall AW and a second port 998 inserted therethrough. A surgical grasping instrument, such as, for example, surgical instrument 1000, is inserted through second port 998. Surgical instrument 1000 is of the type having a handle 1002, an elongate member 1004 extending distally from handle 1002 and terminating in a pair of grasping jaws 1006 and 1008. A trigger 1010 is provided on handle 1002 to operate grasping jaws 1006 and 1008. Housing 906 of surgical stapler 900 is grasped by grasping jaws 1006 and 1008 of surgical instrument 1000 and manipulated such that staple cartridge 912 and anvil 920 are positioned about tissue T.

Figure 28:
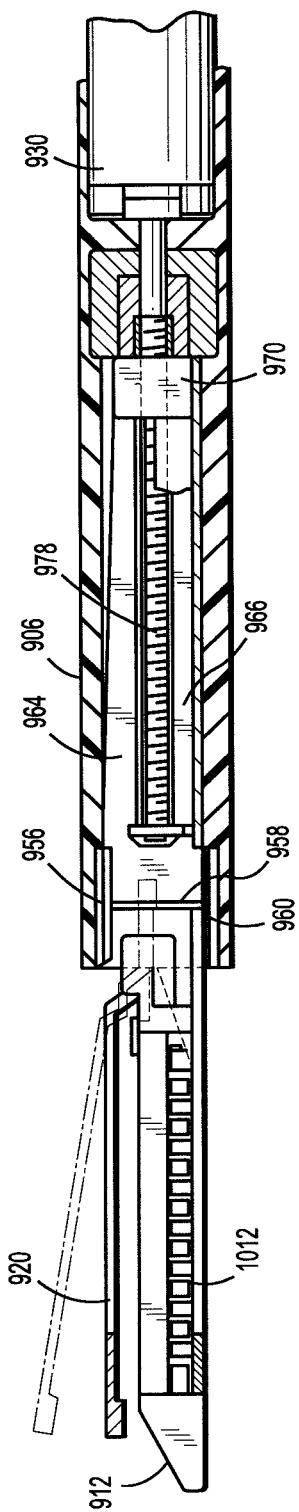
FIG. 28 is a side view, partially shown in section, of the stapler head.
Figure 29:
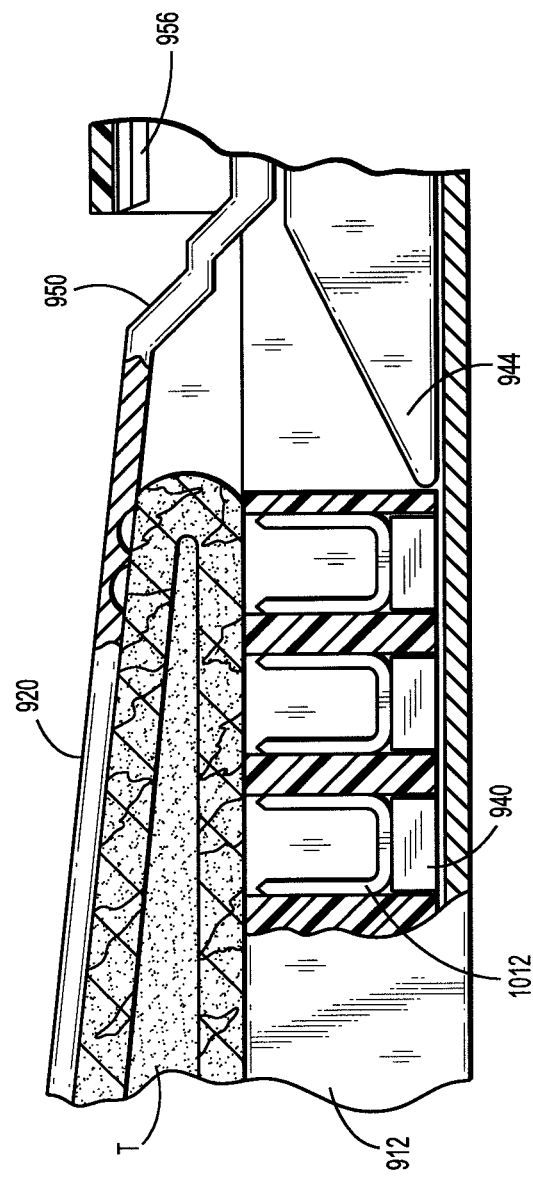
FIG. 29 is an enlarged partial side view of the stapler head positioned about tissue.

Referring now to FIGS. 28 and 29, in the initial position, anvil 920 is in the open position spaced apart from staple cartridge 912. Drive member 970 is in a proximal most position on lead screw 978. Upper beam portion 956 is proximal of angled portion 950 of anvil 920. Distal camming surface 944 is also proximal of pushers 940.

Figure 30:
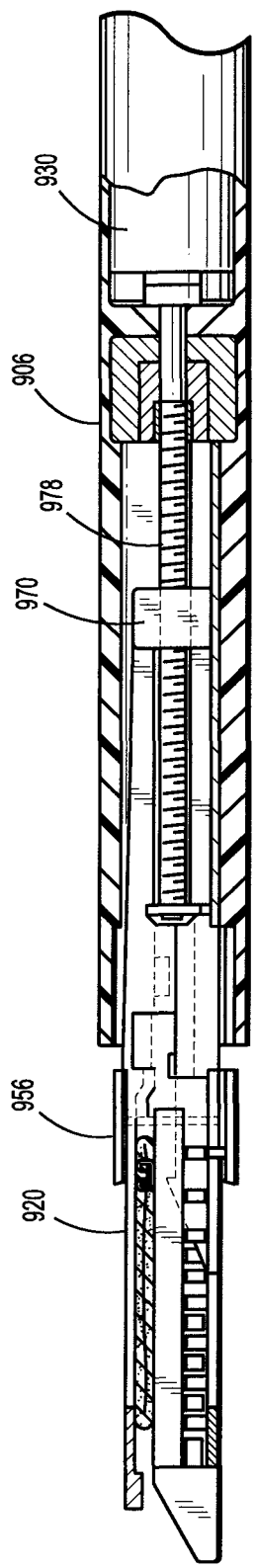
FIG. 30 is a side view, partially shown in section, of the stapler head during initial actuation.
Figure 31:
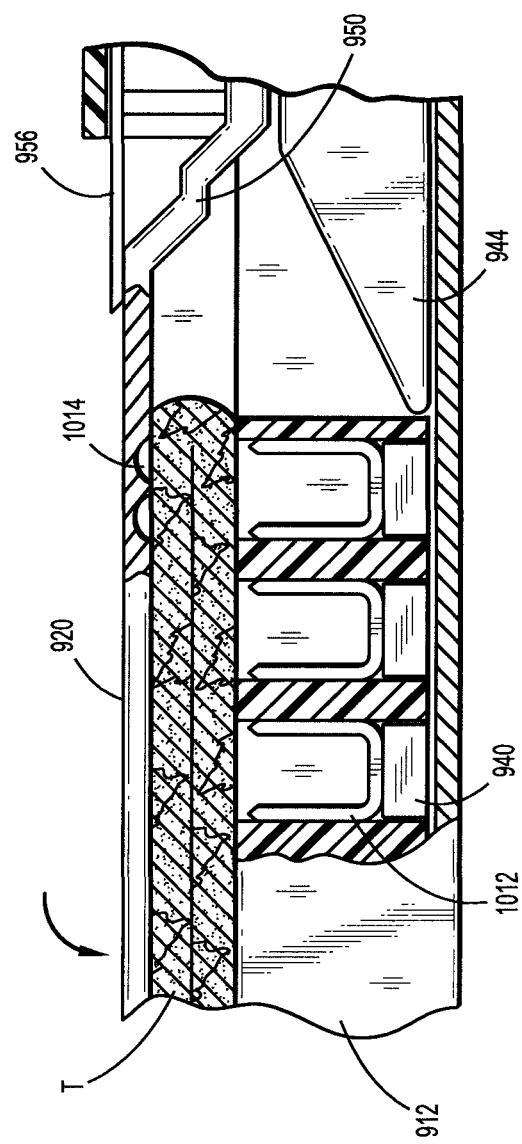
FIG. 31 is an enlarged partial side view of the stapler head during initial actuation to capture tissue.

Referring now to FIGS. 27 and 30 and 31, upon actuation of control button 924 (FIG. 27) motor assembly 930 is actuated to rotate lead screw 978 thereby initiating distal movement of drive member 970. As drive member 970 moves distally, upper beam portion 956 engages angled portion 950 on anvil 920 moving anvil 920 to the closed position and securing tissue T between anvil 920 and staple cartridge 912.

Referring now to FIGS. 32 and 33, as drive member 970 is moved to the distal most position along lead screw 978, distal camming surface 944 engages pusher 940 driving staples such as, for example, staples 1012 upward into staple crimping pockets 1014 formed in anvil 922 thereby staple tissue T. Thus, it can be seen that the use of surgical stapler 900 allows a high degree of flexibility relative to the tissue being operated upon by positioning motor assembly 930 of surgical stapler 900 adjacent staple assembly 908 and connected to handle 902 by flexible elongate member 904.

Referring now to FIGS. 34-37, there is disclosed a further alternative embodiment of a surgical stapler having a remote staple head 1110. Surgical stapler 1110 includes a handle 1112 having an elongate flexible member 1114 extending distally from handle 1112. A housing assembly 1116 and a staple assembly 1118 extend distally from elongate flexible member 1114. Surgical stapler of 1110 includes additional degrees of flexibility in that housing assembly 1116 includes an articulating section 1120 positioned between a proximal portion 1122 and a distal portion 1124 of housing assembly 1116.

Similar to those embodiments described hereinabove, staple assembly 1118 includes a channel member 1126 supporting a staple cartridge 1128. Staple cartridge 1128 includes rows of staple pockets 1130 and 1132. A knife slot 1134 extends through staple cartridge 1128. An anvil 1136 is pivotally mounted to channel member 1126 and is movable between an open position spaced from staple cartridge 1128 to a closed position adjacent staple cartridge 1128. Anvil 1136 includes an anvil slot 1138. A control button 1140 is provided on handle 1112 to actuate staple assembly 1118 in a manner similar to that described hereinabove with respect to surgical stapler 900.

Figures 34, 35:
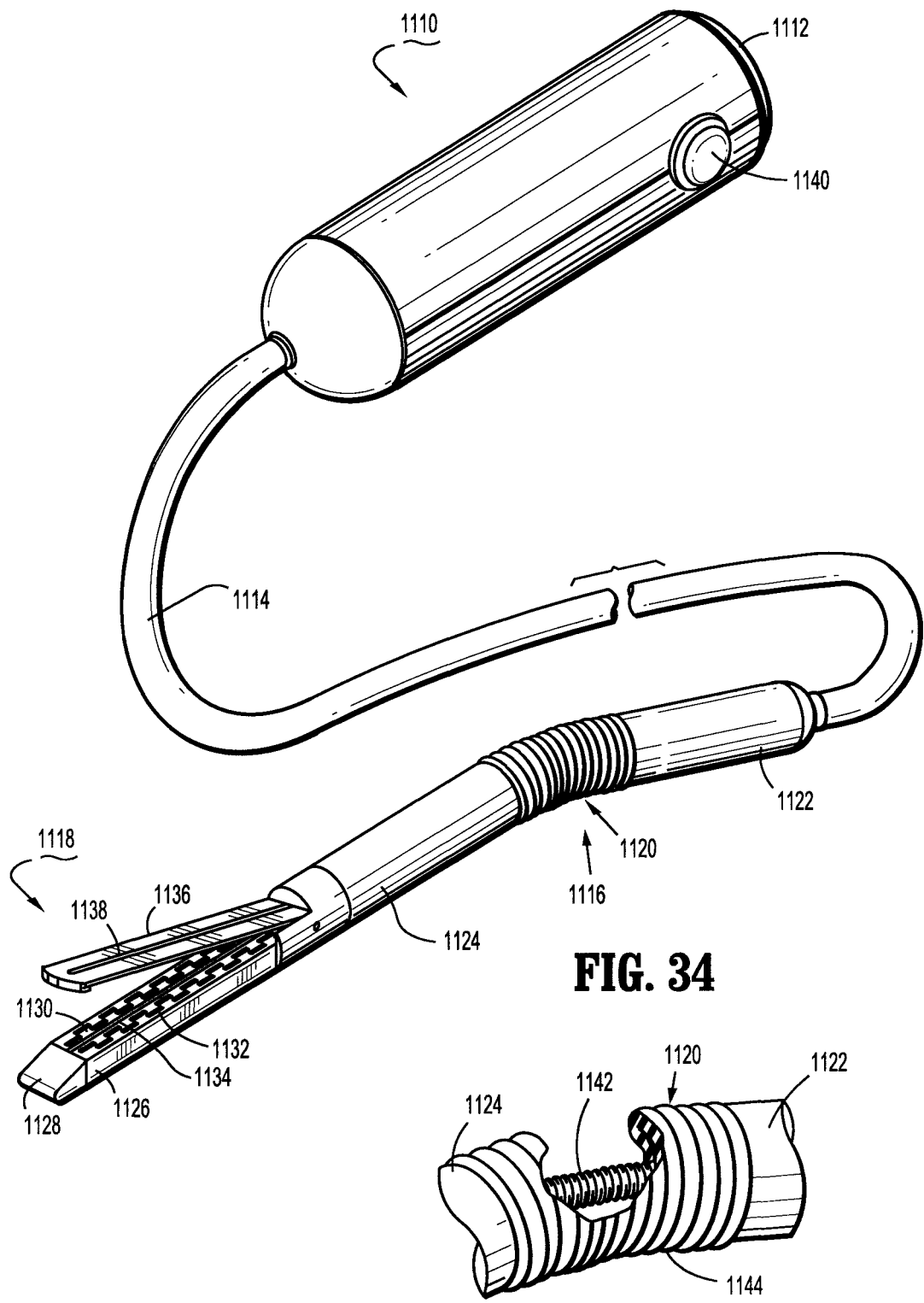
FIG. 34 is a perspective view of another embodiment of a surgical stapler with a motor in the stapler head.
FIG. 35 is an enlarged view, partially shown in section, of an articulation segment in the stapler head of FIG. 34.

Referring for the moment to FIG. 35, articulating section 1120 incorporates a flexible drive or lead screw 1142 and a flexible cover 1144. The provision of articulating section 1120 allows distal portion 1124 of housing assembly 1116 to be manipulated relative to proximal portion 1122 of housing assembly 1116.

Figure 36:
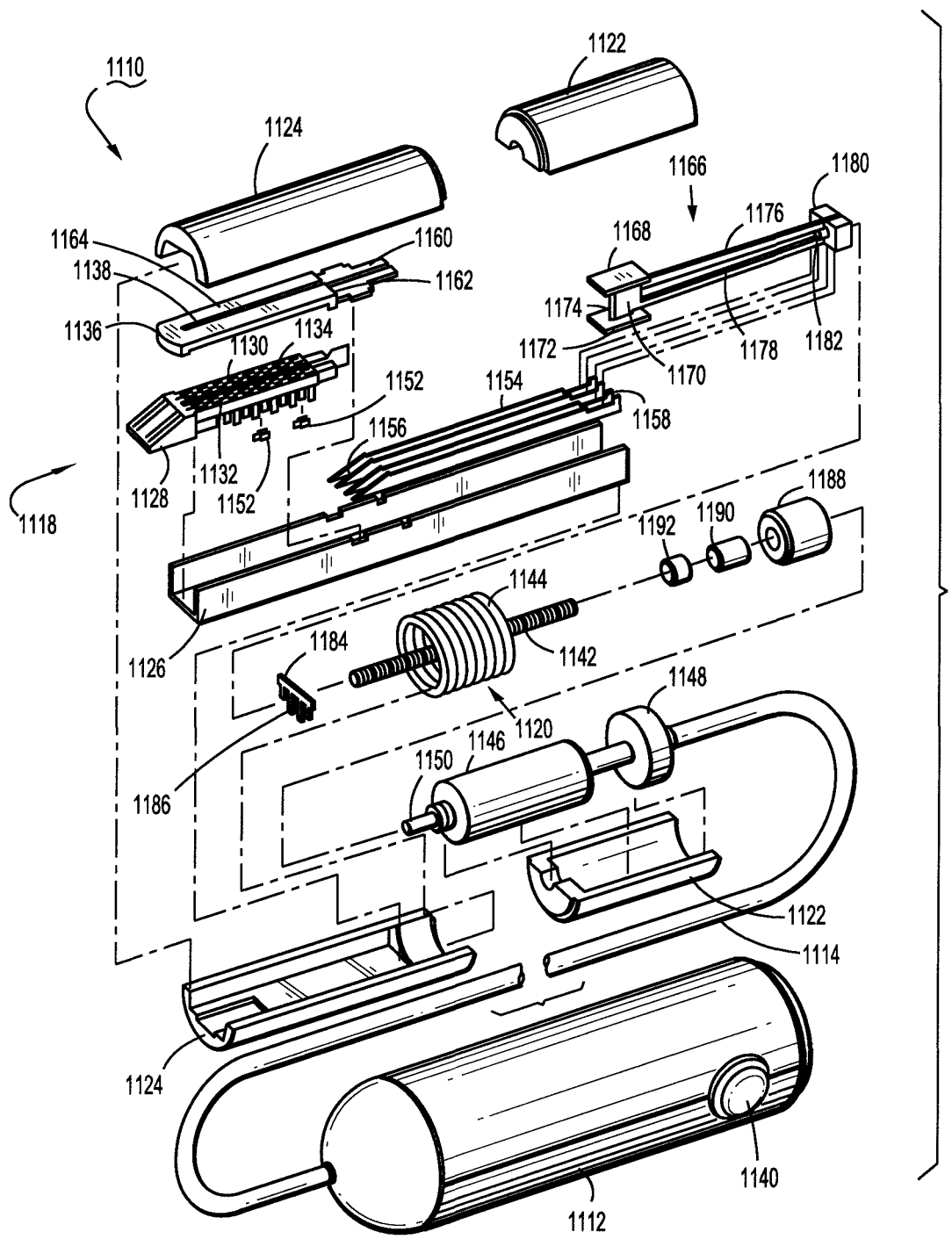
FIG. 36 is a perspective view, with parts separated, of the surgical stapler of FIG. 34.

Referring now to FIG. 36, the components of surgical stapler 1110 will now be described. It should be noted that, with the exception of articulating section 1120 including flexible drive member 1142 and flexible cover 1144, all the following listed components are constructed, assembled and function identical to the corresponding components described hereinabove with respect to surgical stapler 900. Surgical stapler 1110 includes a motor assembly 1146 located within proximal portion 1122 of housing assembly 1116. A gasket 1148 is provided to seal motor assembly 1146 within proximal portion 1122. Motor assembly 1146 includes a keyed drive shaft 1150.

Staple assembly 1118 includes pushers 1152 located within staple cartridge 1128. Camming bars 1154 are provided to engage pushers 1152 and include distal camming surfaces 1156 and proximal engagement notches 1158.

Anvil 1136 includes a proximal portion 1160 secured to channel member 1126 and an angled portion 1162. A longitudinal distal portion 1164 extends from angled portion 1162. A camming beam 1166 is provided and includes an upper beam portion 1168, a central web portion 1170 and a lower beam portion 1172. A cutting blade 1174 is provided on central web portion 1170. Camming beam 1166 additionally includes upper beam extension 1176 and lower beam extension 1178. A drive member 1180 is provided and includes a threaded bore 1182 for receipt of flexible lead screw 1142. A support gate 1184 is positioned within channel member 1126 and includes a hole 1186 for support of flexible lead screw 1142.

An outer support hub 1188, intermediate support hub 1190 and an inner engagement hub 1192 are provided to connect motor assembly 1146 to flexible lead screw 1142.

It should be noted that motor assembly 1146 is provided within proximal portion 1122 of housing assembly 1116 while staple assembly 1118 and camming beam 1166 are located within distal portion 1124 of housing assembly 1116.

Figure 37:
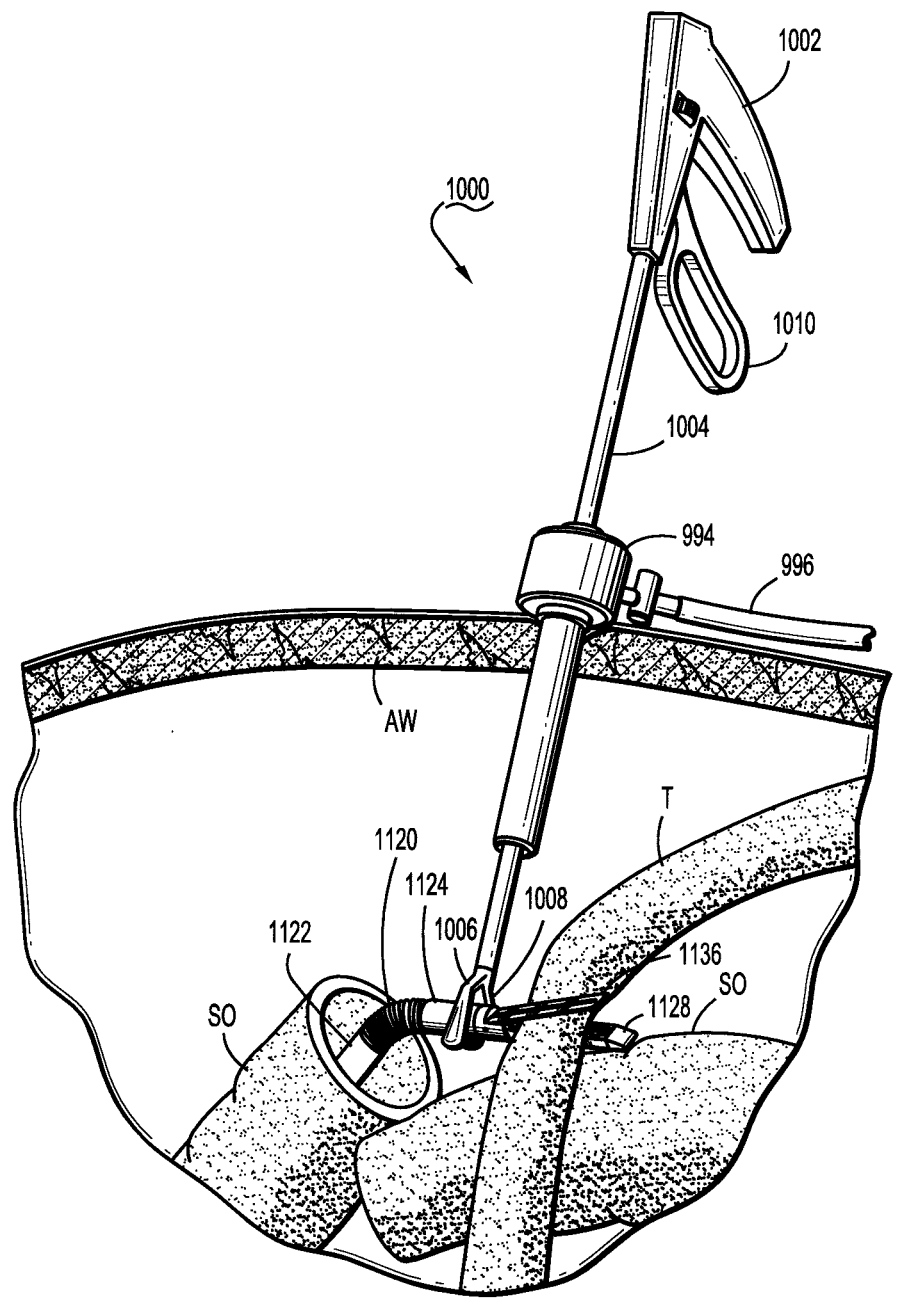
FIG. 37 is a perspective view of the surgical stapler of FIG. 34 in use.

Referring now to FIG. 37, surgical stapler of 1110 is particularly suited for use in surgical procedures where a surgical stapling devices can be inserted through an auxiliary or supplemental organ SO to access the tissue T to be operated upon. In order to manipulate staple cartridge 1128 and anvil 1136 with respect to tissue T, an incision is made through the abdominal wall AW of a patient and a first port 994 is inserted therethrough. A source of insufflation fluid 996 may be used to create a working space within the body cavity.

Thereafter, surgical grasping instrument 1000 may be inserted through first port 994 to position first and second jaws 1006 and 1008 about a portion of surgical stapler 1110. For example, as shown, first and second jaws 1006 and 1008 grasp distal portion 1124 and manipulate distal portion 1124 relative to proximal portion 1122 by bending articulating section 1120. As noted hereinabove, articulating section 1120 includes flexible lead screw 1142 which allows for the transmission of power from motor assembly 1146 to staple assembly 1118 through an angle. Additionally, flexible cover 1144 of articulating section 1120 allows distal portion 1124 to be manipulated relative to proximal portion 1122 of housing assembly 1116. Once anvil 1136 and staple cartridge 1128 have properly been positioned about the tissue T to be operated upon, surgical stapler 1110 may be actuated by control button 1140 (FIG. 34) to actuate staple assembly 1118 in a manner substantially identical to that described hereinabove with surgical stapler 900 to apply rows of staples to tissue T and sever tissue T between the rows of staples.

Figures 38, 39:
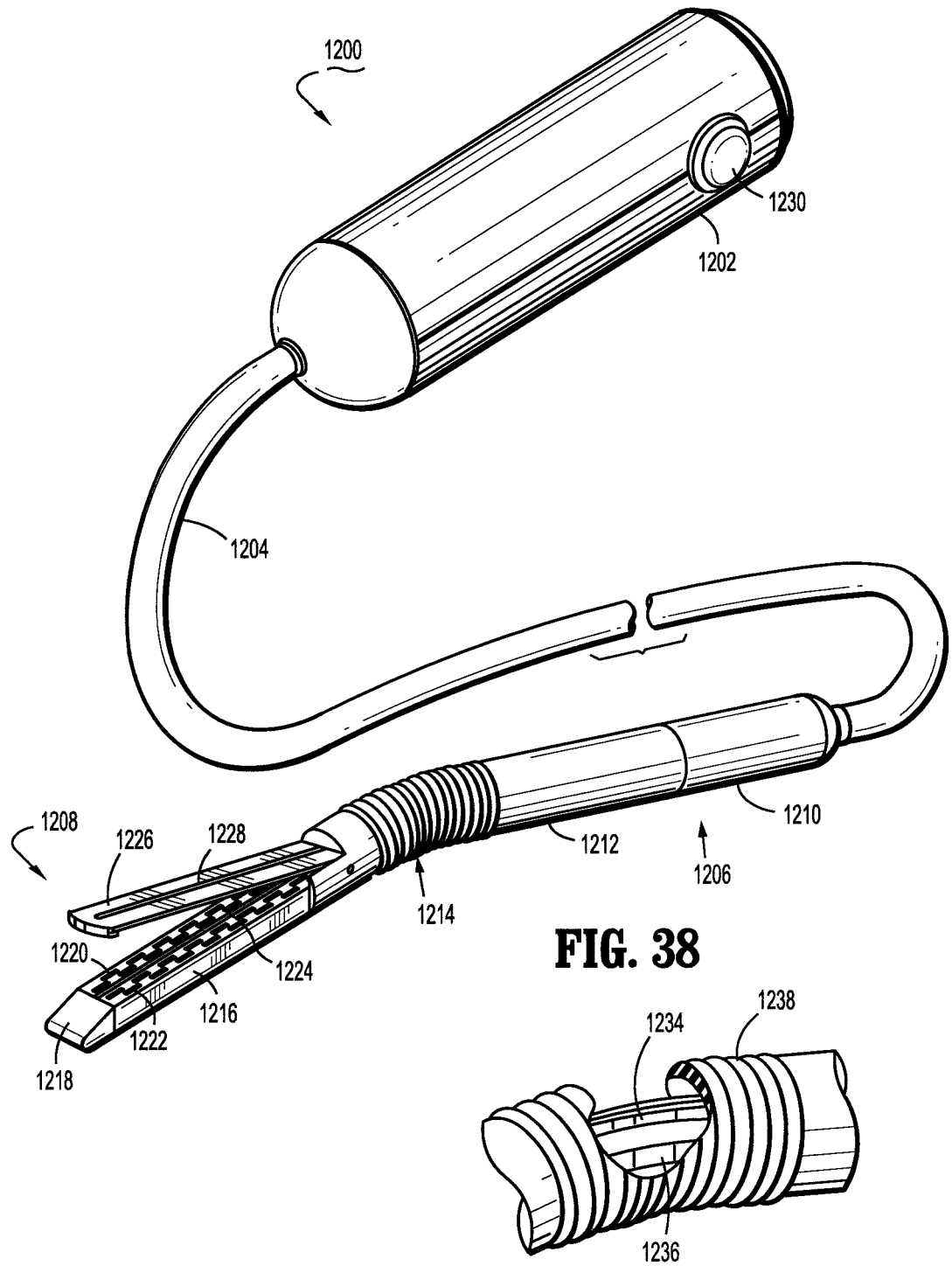
FIG. 38 is a perspective view of a further embodiment of a surgical stapler having a motor in a stapler head.
FIG. 39 is an enlarged view, partially shown in section, of an articulation segment of the surgical stapler of FIG. 38.

Referring now to FIGS. 38-41, and initially with regard to FIG. 38, there is disclosed a further alternative embodiment of a surgical stapler with a remote motor in the head 1200 for use in surgical procedures. Surgical stapler 1200 is similar to surgical stapler 1110 described hereinabove and generally includes a handle 1202 having a flexible elongate member 1204 extending therefrom. A housing assembly 1206 and a staple assembly 1208 extend from flexible elongate member 1204. Housing assembly 1206 includes a proximal portion 1210, and intermediate portion 1212, and an articulating distal portion 1214. Staple assembly 1208 extends from articulating distal portion 1214.

Staple assembly 1208 includes a channel member 1216 supporting a staple cartridge 1218. Staple cartridge 1218 includes staple pockets 1220 and 1222 and a knife slot 1224 intermediate staple pockets 1220 and 1222. And anvil 1226 is pivotally attached to channel member 1216 and includes an anvil slot 1228. A control button 1230 is provided on handle 1202 to actuate staple assembly 1208.

Referring for the moment to FIG. 39, articulating distal portion 1214 includes flexible upper and lower beam extensions 1234 and 1236 and a flexible cover 1238. Articulating distal portion 1214 allows staple assembly 1208 to be manipulated relative to intermediate portion 1212.

Figure 40:
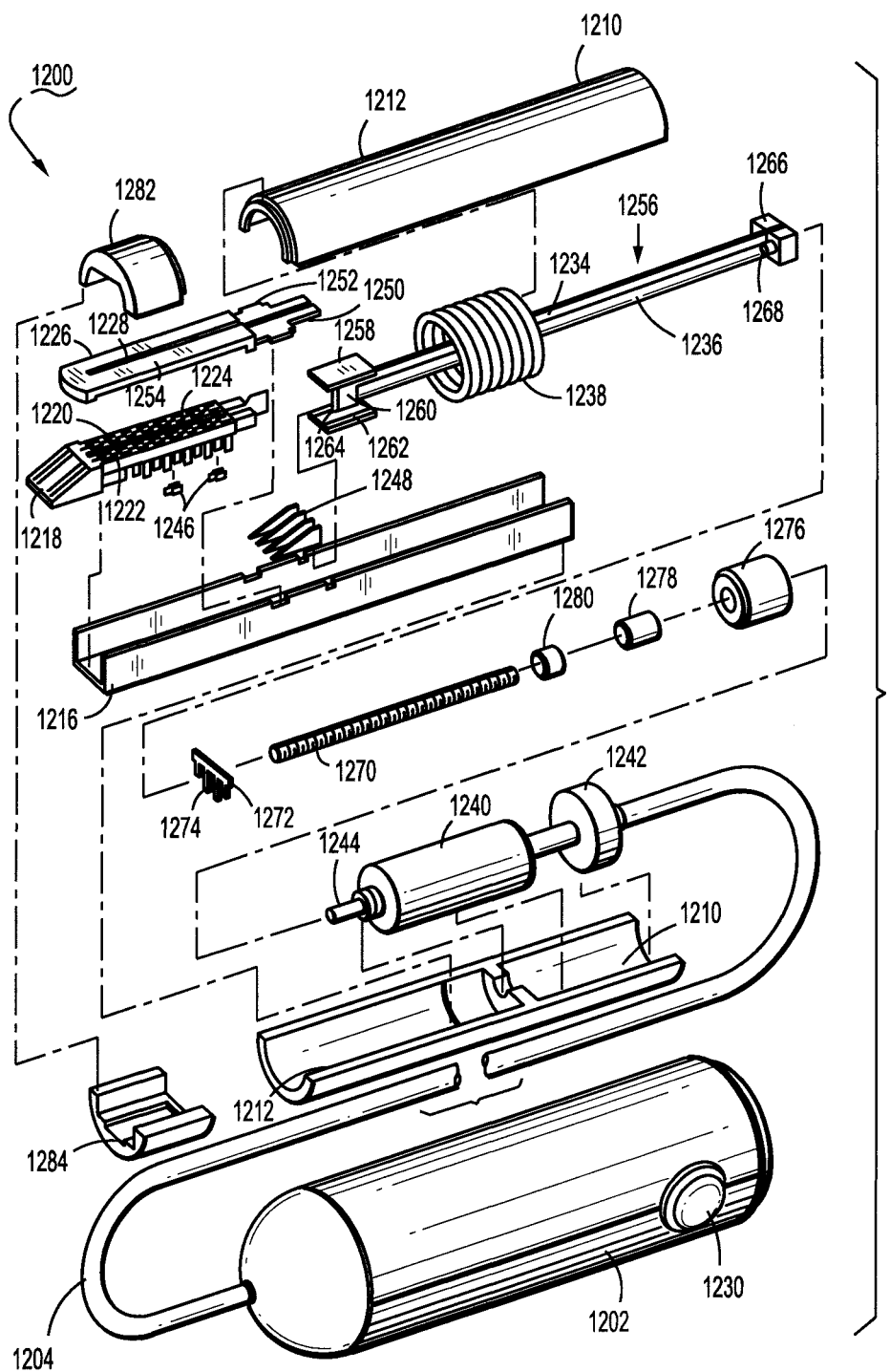
FIG. 40 is a perspective view, with parts separated, of the surgical stapler of FIG. 38.

Referring now to FIG. 40, the components of surgical stapler 1200 will now be described. It should be noted that, except where indicated with regard to articulating distal portion 1214 and camming bars 1248, all of the following components are constructed, assembled in function identical to that described hereinabove with respect to surgical stapler 900. Surgical stapler 900 additionally includes a motor assembly 1240 positioned within proximal portion 1210 of housing assembly 1206. A gasket 1242 is provided to seal motor assembly 1240 within proximal portion 1210. Motor assembly 1240 includes a keyed drive shaft 1244.

Staple cartridge 1218 includes pushers 1246 to eject staples 62, 64 (FIG. 4) out of staple pockets 1220 and 1222. In contrast to camming bars 942 described hereinabove with respect to surgical stapler 900, surgical stapler 1200 includes abbreviated camming bars 1248 for engagement with pushers 1246.

Anvil 1226 includes a proximal portion 1250 affixed to channel member 1216, and angled portion 1252 and an elongated distal portion 1254. A camming beam 1256 is provided and includes an upper beam portion 1258, a central web portion 1260 and a lower beam portion 1262. A cutting blade 1264 is formed on central web portion 1260. As noted hereinabove, camming beam 1256 includes upper and lower flexible beam extensions 1234 and 1236 allowing camming beam 1256 to bend as it passes through articulating portion 1214. Camming beam 1256 additionally includes a drive member 1266 having a threaded bore 1268. Threaded bore is configured to receive lead screw 1270. A support gate 1272 is positioned within channel member 1216 and includes a hole 1274 for passage of lead screw 1270.

Surgical stapler 1200 additionally includes an outer support hub 1276, and intermediate support hub 1278 and inner engagement hub 1280. A pair of channel end caps 1282 and 1284 are provided about channel member 1216 to support channel member 1216 relative to flexible cover 1238.

Figure 41:
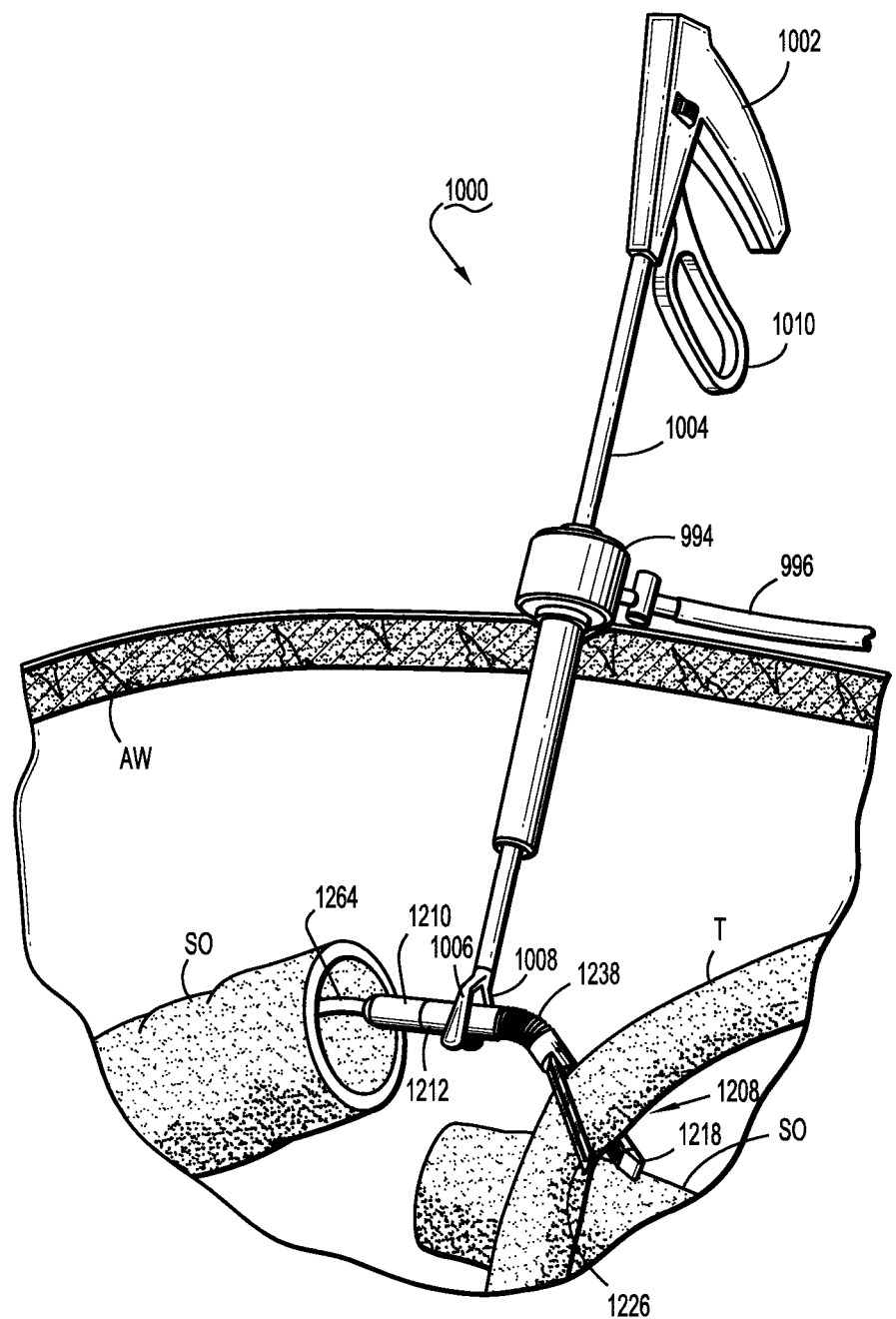
FIG. 41 is a perspective view of the surgical stapler of FIG. 38 in use.

Referring now to FIG. 41, the use of surgical stapler 1200 to stapler tissue T will now be described. The procedure is performed in a manner similar to that described hereinabove with respect to surgical stapler 1110. Surgical stapler 1200 is inserted through a supplemental organ SO to position staple assembly 1208 in the vicinity of tissue T. An incision is made through the abdominal wall AW and a first port 944 is inserted therethrough. Thereafter, the abdominal cavity is insufflated with a source of insufflation fluid 996 to create a working space within the body cavity. Surgical instrument 1000 is inserted through first port 944 to position first and second jaws 1006 and 1008 about a portion of housing assembly 1206, for example, about intermediate portion 1212. Thereafter, surgical instrument 1000 is manipulated to position anvil 1226 and staple cartridge 1218 about tissue T. Surgical stapler 1200 is actuated via control button 1230 (FIG. 38) to staple tissue T in a manner substantially identical to that described hereinabove with respect to surgical stapler 900.

Thus, the disclosed surgical staplers including a highly flexible elongate member and, in some instances, further articulation within a housing adjacent to staple assembly allow for a high level of manipulation within the body cavity.

It will be understood that various modifications may be made to the embodiments disclosed herein. For example, various other components may be made of flexible materials, such as, for example, the camming bars, the channel member etc. to enhance the flexibility of the surgical instrument. Further, as noted hereinabove the disclosed auxiliary collar and handle assembly may be used with various other types of surgical instruments including biopsy devices, clip appliers, etc. Therefore, the above description should not be construed as limiting, but merely as exemplifications of particular embodiments. Those skilled in the art will envision other modifications within the scope and spirit of the claims appended hereto.

What is claimed is:

1. A surgical stapler, comprising:
    an elongate member; and
    a stapler head positioned at a first end of the elongate member, the stapler head including:
        a housing including a motor disposed therein;
        a staple assembly positioned distally of the housing;
        a drive member operably coupled to the staple assembly;
        an articulating section extending between and interconnecting the housing and the staple assembly, the articulating section selectively articulatable to articulate the staple assembly relative to the housing; and
        a flexible member extending through the articulating section, the flexible member operably coupling the motor with the drive member, wherein the motor is configured to rotate the flexible member, and wherein rotation of the flexible member, in turn, translates the drive member through the staple assembly.

2. The surgical stapler according to claim 1, wherein the staple assembly includes a staple cartridge configured to retain surgical staples therein and an anvil assembly, at least one of the anvil assembly or the staple cartridge movable with respect to the other between an open position and a closed position.

3. The surgical stapler according to claim 2, wherein translation of the drive member through the staple assembly moves the anvil assembly from the open position to the closed position and fires the surgical staples from the staple cartridge.

4. The surgical stapler according to claim 1, wherein the flexible member is a lead screw and wherein the drive member is threadably disposed about the lead screw.

5. The surgical stapler according to claim 1, further including a handle coupled to a second end of the elongate member.

6. The surgical stapler according to claim 5, further including a control button disposed on the handle and coupled to the motor for selectively rotating the flexible member.

7. The surgical stapler according to claim 1, wherein the articulating section is configured to permit articulation of the staple assembly relative to the housing in at least one plane.

8. The surgical stapler according to claim 1, further including a flexible cover disposed about the articulating section.

9. The surgical stapler according to claim 1, wherein at least a portion of the elongate member is flexible.

10. The surgical stapler according to claim 1, wherein the flexible member is configured to flex to conform to an articulated position of the articulating section.

11. A surgical stapler, comprising:
    an elongate member having a first end and a second end;
    a handle coupled to the first end of the elongate member; and
    a stapler head coupled to the second end of the elongate member, the stapler head including:
        a housing including a motor disposed therein;
        a staple assembly including a staple cartridge configured to retain surgical staples therein and an anvil assembly pivotably coupled to the staple cartridge;
        a drive member selectively translatable through the staple assembly for moving the anvil assembly relative to the staple cartridge from an open position to a closed position and for firing the surgical staples from the staple cartridge;
        an articulating section interconnecting the housing and the staple assembly, the articulating section configured to permit articulation of the staple assembly relative to the housing; and
        a flexible member extending through the articulating section, the flexible member operably coupled to the motor proximally of the articulating section and having the drive member coupled thereto distally of the articulating section, wherein the motor is configured to rotate the flexible member, and wherein rotation of the flexible member, in turn, translates the drive member through the staple assembly.

12. The surgical stapler according to claim 11, further including a control button disposed on the handle and coupled to the motor for selectively rotating the flexible member.

13. The surgical stapler according to claim 11, wherein the articulating section is configured to permit articulation of the staple assembly relative to the housing in at least one plane.

14. The surgical stapler according to claim 11, further including a flexible cover disposed about the articulating section.

15. The surgical stapler according to claim 11, wherein at least a portion of the elongate member is flexible.

16. The surgical stapler according to claim 11, wherein the flexible member is configured to flex to conform to an articulated position of the articulating section.

17. The surgical stapler according to claim 11, wherein the flexible member is a lead screw and wherein the drive member is threadably disposed about the lead screw.

* * * * *